United States Patent
Tamburrino et al.

(10) Patent No.: US 10,240,164 B2
(45) Date of Patent: Mar. 26, 2019

(54) TRANSGENIC PLANTS HAVING ALTERED LIGNIN DENSITY

(71) Applicant: British American Tobacco (Investments) Limited, London (GB)

(72) Inventors: Juan Pablo Sanchez Tamburrino, London (GB); Kieron Edwards, London (GB); Maria Eriksson, Umea (SE)

(73) Assignee: British American Tobacco (Investments) Limited, London (GB)

( * ) Notice: Subject to any disclaimer, the term of this patent is extended or adjusted under 35 U.S.C. 154(b) by 0 days.

(21) Appl. No.: 14/650,190

(22) PCT Filed: Dec. 4, 2013

(86) PCT No.: PCT/GB2013/053205
§ 371 (c)(1),
(2) Date: Jun. 5, 2015

(87) PCT Pub. No.: WO2014/087159
PCT Pub. Date: Jun. 12, 2014

(65) Prior Publication Data
US 2015/0307893 A1 Oct. 29, 2015

(30) Foreign Application Priority Data
Dec. 5, 2012 (GB) .................................. 1221883.0

(51) Int. Cl.
C12N 15/82 (2006.01)
A01H 5/12 (2018.01)
A24B 13/00 (2006.01)

(52) U.S. Cl.
CPC ........... *C12N 15/8255* (2013.01); *A01H 5/12* (2013.01); *A24B 13/00* (2013.01); *C12N 15/8216* (2013.01); *C12N 15/8218* (2013.01)

(58) Field of Classification Search
None
See application file for complete search history.

(56) References Cited

U.S. PATENT DOCUMENTS

2009/0276912 A1* 11/2009 Sherman .............. C07K 14/415
800/264

FOREIGN PATENT DOCUMENTS

| CN | 101302523 A | 11/2008 |
|---|---|---|
| EP | 0116718 A1 | 8/1984 |
| EP | 0242246 A1 | 10/1987 |
| EP | 0270822 A1 | 6/1988 |
| EP | 0369637 A2 | 5/1990 |
| GB | 2197653 A | 5/1988 |
| WO | 97/49811 A1 | 12/1997 |
| WO | 200009658 A2 | 2/2000 |
| WO | 2009/104181 A1 | 8/2009 |
| WO | 2010/075143 A1 | 7/2010 |
| WO | WO2010075143 * | 7/2010 ............. C12N 15/82 |

OTHER PUBLICATIONS

Rogers et al 2005 Journal of Experimental Botany 56:1651-1663.*
Takata et al 2008 GenBank Accessions AB429411, AB429410, alignment included in body of rejection.*
Dauwe R. et al., Molecular phenotyping of lignin-modified tobacco reveals associated changes in cell-wall metabolism, primary metabolism, stress metabolism and photorespiration, The Plant Journal (2007), vol. 52, issue 2, pp. 263-285.
Busov, V., Perennial challenges and opportunities, New Phytologist, vol. 176, issue 1, pp. 3-6, 2007.
Wang, Zhi-Yong et al., Constitutive Expression of the Circadian Clock Associated 1 (CCA1) Gene Disrupts Circadian Rhythms and Suppresses Its Own Expression, Cell, vol. 93, pp. 1207-1217, Jun. 26, 1998.
Mizoguchi, T. et al., LHY and CCA1 Are Partially Redundant Genes Required to Maintain Circadian Rhythms in *Arabidopsis*, Developmental Cell, vol. 2, No. 5, pp. 629-641, May 2002.
Serikawa, M. et al., Functional Conservation of Clock-Related Genes in Flowering Plants: Overexpression and RNA Interference Analyses of the Circadian Rhythm in the Monocotyledon Lemna gibba, Plant Physiology, Apr. 2008, vol. 146, No. 4, pp. 1952-1963.
Sticklen, M. B., Plant genetic engineering for biofuel production: towards affordable cellulosic ethanol, Nature Reviews|Genetics, vol. 9, Jun. 2008, pp. 433-443.
Green, R. M. et al., Loss of the circadian clock-associated protein 1 in *Arabidopsis* results in altered clock-regulated gene expression, Proc. Natl. Acad. Sci. USA, vol. 96, pp. 4176-4179, Mar. 1999.

(Continued)

*Primary Examiner* — Brent T Page
(74) *Attorney, Agent, or Firm* — McKee, Voorhees & Sease, PLC

(57) ABSTRACT

The present invention relates to a method of modulating the density of lignin in a test plant compared to the corresponding lignin density in a wild-type plant cultured under the same conditions, the method comprising modulating the concentration and/or activity of a polypeptide encoded by a core circadian clock gene, wherein modulation of the concentration and/or activity of the polypeptide modulates lignin density in the test plant. The present invention further relates to the use of a genetic construct which is capable of modulating the concentration and/or activity of a polypeptide encoded by a core circadian clock gene, for modulating the density of lignin in a plant, wherein the genetic construct encodes a polypeptide comprising the amino acid sequence substantially as set out in SEQ ID No's: 2 or 4, or a functional variant or fragment thereof. In addition the present invention relates to a plant host cell comprising a genetic construct which is capable of modulating the concentration and/or activity of a polypeptide encoded by a core circadian clock gene is also taught.

22 Claims, 13 Drawing Sheets
Specification includes a Sequence Listing.

(56) References Cited

OTHER PUBLICATIONS

Lu, S. X. et al. Circadian Clock Associated1 and Late Enlongated Hypocotyl Function Synergistically in the Circadian Clock of *Arabidopsis*, Plant Physiology, Jun. 2009, vol. 150, pp. 834-843.
Alabadi, D. et al., Critical Role for CCA1 and LHY in Maintaining Circadian Rhythmicity in *Arabidopsis*, Current Biology, vol. 12, No. 9, pp. 757-761, Apr. 30, 2002.
Ibanez, C. et al., Circadian Clock Components Regulate Entry and Affect Exit of Seasonal Dormancy as Well as Winter Hardiness in Populus Trees, Plant Physiology, vol. 153, No. 4, pp. 1823-1833, Aug. 2010.
Bevan, M., Binary Agrobacterium vectors for plant transformation, Nucleic Acids Research, 1984, vol. 12, pp. 8711-8721.
Chang, S. et al., A Simple and Efficient Method for Isolating RNA from Pine Trees, Plant Molecular Biology Reporter, vol. 11(2), 1993, pp. 113-116.
Edwards K. D. et al., Flowering Locus C Mediates Natural Variation in the High-Temperature Response of the *Arabidopsis* Circadian Clock, The Plant Cell, vol. 18, pp. 639-650, Mar. 2006.
Edwards, K. D. et al., Quantitative analysis of regulatory flexibility under changing environmental conditions, Molecular Systems Biology 6:424, 2010.
Eriksson, M. E. et al., Increased gibberellin biosynthesis in transgenic trees promotes growth, biomass production and xylem fiber length, Nature Biotechnology, vol. 18, Jul. 2000, pp. 784-788.
Helliwell, C. A. et al., High-throughput vectors for efficient gene silencing in plants, Functional Plant Biology, 2002, 29, pp. 1217-1225.
Horsch R. B. et al., A Simple and General Method for Transferring Genes into Plants, 1985 Science, 227: 1229-1231.
Kozarewa, I. et al., Alteration of PHYA expression change circadian rhythms and timing of bud set in Populus, Plant Molecular Biology (2010), 73:143-156.
Schaffer, R. et al., The late elongated hypocotyl Mutation of *Arabidopsis* Disrupts Circadian Rhythms and the Photoperiodic Control of Flowering, Cell, vol. 93(7), 1219-1229, Jun. 26, 1998.
Takata, N. et al., Molecular phylogeny and expression of poplar circadian clock genes, LHY1 and LHY2, New Phytologist (2009), 181: 808-819.

Thompson, J. D. et al., CLUSTAL W: improving the sensitivity of progressive multiple sequence alignment through sequence weighting, position-specific gap penalties and weight matrix choice, Nucleic Acids Research, 1994, vol. 22, No. 22, pp. 4673-4680.
Thompson, J. D. et al., The CLUSTAL_X windows interface: flexible strategies for multiple sequence alignment aided by quality analysis tools, Nucleic Acids Research, 1997, vol. 25, No. 24, pp. 4876-4882.
van Engelen, F. A. et al., pBINPLUS: an improved plant transformation vector based on pBIN19, Transgenic Research 4, 288-290 (1995).
Eriksson, M. E. et al., The Circadian Clock. A Plant's Best Friend in a Spinning World, Plant Physiology, vol. 132, No. 2, Jun. 2003, pp. 732-738, XP-002719875, abstract The APRR/TOC1 Quintet. Is Their Daily Round Important for Circadian Timing? (pp. 735-736).
Wang, Xintao et al., Robust expression and association of ZmCCA1 with circadian rhythms in maize, Plant Cell Reports, vol. 30, No. 7, Jul. 2011, pp. 1261-1272.
Database UniProt, Mar. 3, 2009, "SubName: Full=PnLHY1 protein; SubName: Full=Transcription factor LHY;", XP002719877, retrieved from EBI accession No. UNIPROT: B7X9P1, Database accession No. B7X9P1.
Database UniProt, Mar. 3, 2009 "SubName: Full=PnLHY2 protein; SubName: Full=Transcription factor LHY;", XP002719878, retrieved from EBI accession No. UNIPROT: B7X9P2, Database accession No. B7X9P2.
Rogers, L. A. et al., "Light, the circadian clock, and sugar perception in the control of lignin biosynthesis", Journal of Experimental Botany, Jun. 2005, vol. 56, No. 416, p. 1651-1663, XP-002719879.
Pan, Yinghong et al., "Cytochrome P450 Monooxgenases as Reporters for Circadian-Regulated Pathways", Plant Physiology, Jun. 2009, vol. 150, No. 2, pp. 858-878, XP-002719880.
International Search Report and Written Opinion, dated May 9, 2014, for PCT/GB2013/053205.
Written Opinion, dated Nov. 7, 2014, for PCT/GB2013/053205.
International Preliminary Report on Patentability, dated Feb. 12, 2015, for PCT/GB2013/053205.
Buchwald, A general bilinear model to describe growth or decline time profiles, Mathematical Biosciences, 2007, 205:108-136.

* cited by examiner

WT (ZT1, Φ 4.3 mm)

WT (ZT19, Φ 4.3 mm)

lhy-10 (ZT1, Φ 4.3 mm)

lhy-10 (ZT19, Φ 4.2 mm)

TRANSGENIC PLANTS HAVING ALTERED LIGNIN DENSITY

CROSS-REFERENCE TO RELATED APPLICATIONS

This application is a U.S. National Stage Application of International Application PCT/GB2013/053205, filed Dec. 4, 2013, which claims priority to G.B. Application No. 1221883.0, filed Dec. 5, 2012, each of which is hereby incorporated by reference in its entirety for all purposes.

INCORPORATION-BY-REFERENCE OF SEQUENCE LISTING

The contents of the text file named "BTMK_292_00US_SeqList_ST25", which was recorded May 29, 2015 and is 20 KB in size, are hereby incorporated by reference in their entireties.

TECHNICAL FIELD

The present invention relates to methods of modulating lignin concentrations in plants. The invention also extends to methods of modulating the concentration and/or activity of polypeptides encoded by circadian core clock genes within transgenic plants. The invention also extends to constructs, which can be used to modulate the polypeptides, plant cells transformed with such constructs, and to transgenic plants themselves. The invention also relates to the use of harvested leaves from such transgenic plants which have been transformed with a genetic construct for modulating lignin density, and smoking articles comprising such leaves.

BACKGROUND

Plants rely on an internal clock in order to regulate the activity of a variety of internal biochemical and physiological processes. This clock is called the circadian rhythm, an important characteristic of which is its cyclical nature. Thus, physiological and biochemical processes regulated by the circadian clock are repeated in cycles, and each cycle is approximately 24 hours long. Molecular studies have revealed that the circadian rhythm is regulated by gene expression and its cyclical nature is due to the activity of autoregulatory negative feedback loops in which one or more gene products repress their own expression.

In addition to the circadian rhythm, plants also rely on external environmental cues, called Zeitgebers, such as light-dark cycles and changes in temperature or humidity, in order to regulate critical developmental processes, for example growth and freezing tolerance. This ability enables plants to acclimatize to a diverse range of climates and environments. Research has revealed that there is an interplay between a plant's circadian rhythm and its ability to respond to environmental cues (i.e. Zeitgebers). Indeed, environmental cues can be used to entrain (i.e. modulate) the length of a plant's circadian rhythm, and the biochemical and physiological processes which they regulate. Therefore, a plant's phenotype may be altered if it is exposed to certain artificial environmental cues.

Lignin is an organic substance responsible for binding cells, fibres and vessels of wood and herbaceous plants. Due to the limited supply of fossil fuels and the increasing demand for alternative forms of energy, lignin is becoming an increasingly important renewable energy resource. However, as lignin is present in growing plants, it helps to preserve the earth's atmosphere by acting as a natural reservoir for greenhouse gases. Accordingly, in order to maintain the balance between the preservation of the earth's environment, and replenishment of lignin, which is used as an energy resource, only a limited number of plants should be harvested for their lignin each year. Unfortunately, this is made difficult by the sub-optimal growth conditions to which plants in a large proportion of the world's forests are exposed. Indeed, trees grown in such sub-optimal conditions tend not to develop fully due to extreme seasonal variations in day length, and so their lignin concentrations are lower than plants grown in standard conditions. There is therefore a need to increase the lignin content of plants which are used as a renewable energy resource, especially plants which are usually exposed to poor growth conditions.

Lignin is also a prominent constituent of tobacco plants, the leaves of which are commonly used in smoking articles, such as cigarettes and cigars. When combusted, the lignin within cured tobacco leaves, undergoes a process called pyrolysis, and releases natural chemicals which may be inhaled during the smoking process. Some of these released chemicals contribute to the smoky flavour produced during the smoking process. While some users may find that these chemicals enhance the smoking experience, others can find that they can compromise the flavour of the inhaled smoke. Accordingly, there is also a need to reduce the lignin content of plants, and particularly their leaves, which are smoked, such as tobacco.

As described in the Examples, the inventors set out to investigate if there was a link between the circadian rhythm and the density of lignin within various plant species, with the aim of controlling plant lignin density. Their research prompted them to create two transgenic Poplar plant line cell lines, the first of which exhibited reduced expression of the core clock genes, LHY1 and LHY2, compared to its wild-type counterpart grown under the same conditions, and the second of which exhibited an enhanced expression of the core clock genes compared to its wild-type counterpart also grown under the same conditions. Global gene expression, growth and lignin density, among other characteristics of these transgenic plants, were then assessed.

SUMMARY OF INVENTION

According to a first aspect of the invention, there is provided a method of modulating the density of lignin in a test plant compared to the corresponding lignin density in a wild-type plant cultured under the same conditions, the method comprising modulating the concentration and/or activity of a polypeptide encoded by a core circadian clock gene, wherein modulation of the concentration and/or activity of the polypeptide modulates lignin density in the test plant.

The inventors were surprised to observe that lignin density in a plant is closely linked to the plant's circadian clock. Thus, advantageously, the inventors have demonstrated that it is possible to influence the density and the concentration of lignin in a test plant by manipulating the concentration and/or activity of proteins that are involved in the circadian clock. The inventors believe that the ability to modulate a plant's lignin density will have far-reaching applications depending on whether one wishes to increase or decrease lignin density in a plant. For example, increasing plant lignin concentration will be useful where lignin is harvested from plants as a source of energy. Clearly, the higher the density of lignin in a harvested plant, the better. Conversely, decreasing plant lignin concentration will have significant utility in plants (and especially their leaves), which can be smoked, such as tobacco, in order to improve the flavour of the inhaled smoke.

It will be appreciated that a core circadian clock gene can be any gene encoding a protein which plays a central role in generating and/or regulating the circadian rhythm of a plant. Core circadian clock genes form self-sustained, interconnected feedback loops that oscillate with a period of approximately 24 hours. One or more genes within this network may exhibit increased (or decreased) expression in response to environmental cues to set the phase of the core circadian clock relative to the external environment. The core clock regulates the expression of other clock-regulated genes via output pathways. Clock regulated genes are genes whose expression shows a rhythm with a period of approximately 24 hours, but are not involved in regulation of the core clock.

The core circadian clock gene may be selected from a group of circadian clock genes consisting of LATE ELONGATED HYPOCOTYL (LHY1 or LHY2); CIRCADIAN CLOCK ASSOCIATED 1 (CCA1); TOC1; G1; PRR3; PRR5; PRR7; PRR9; ELF3; ELF4; TIC; and LUX.

As shown in Table 1, the inventors observed that some core circadian clock genes consistently exhibit one or more phases of expression during 24-hour cycles, and these genes are referred to as rhythmically expressed genes. For example, in poplar plants, the LHY2 gene exhibits a peak in expression which occurs approximately between zeitgeber time (ZT) 3.856 hours and ZT 4.56 hours, as shown in Table 1.

In one embodiment, therefore, the core circadian clock gene may be a rhythmically expressed gene, i.e. can consistently exhibit one or more phases of expression during 24 hour cycles of growth, dependent on the environmental cues (zeitgebers) provided (Edwards et al., 2010. Molecular Systems Biology, 6:424). Preferably, the rhythmically expressed gene is capable of regulating the expression of a clock-regulated gene.

In one embodiment, the core circadian clock gene may be LATE ELONGATED HYPOCOTYL (LHY), which will be known to the skilled technician (Schaffer R et al., 1998. Cell, 93(7): 1219-29). The LATE ELONGATED HYPOCOTYL 1 and 2 genes (LHY1 and LHY2) are expressed in plants and code for MYB domain transcription factors which regulate the transcription of circadian rhythm regulated genes. Molecular studies on *Populus tremula* have identified two homologs, LHY1 and LHY2, as core circadian clock genes which enable poplar plants to adapt to their local environment by regulating the expression of other rhythmically expressed genes and altering their perception of photoperiod (day length). Both genes are homologs of the *Arabidopsis* gene, LHY. The peptides, LHY1 and LHY2, are important for aligning major growth events with long days and warm temperatures in spring and summer, and the ability to obtain freezing tolerance during dormant periods (Ibanez et al., 2010, Plant Physiology, 53: 1823-1833).

Accordingly, in one embodiment, the core circadian clock gene may be LATE ELONGATED HYPOCOTYL 1 (LHY1). The cDNA sequence encoding LHY1, in poplar plants, is 2379 base pairs long, and is referred to herein as SEQ ID NO.1, as follows.

[SEQ ID NO. 1]
```
ATGGGTTGTGGGATAAAGTGGGACAATTGGATTACTGAGTTGGAGAAGGAGGCTGTTGCTAAAGGTG

TTCCGATAGGAAAAGCACTTGAAATAGACATTCCACCACCACGTCCCAAAAGGAAACCAAGCAATCC

TTATCCTCGAAAGACAGGTGTGGGTCCTCCCGCATCACAGGCAGGAGCAAAGGATGGAAAGCTTTTA

ACTTCAACTTCTTCTCCACATTGTAGGAAAGTTTTAGATTTGGAGAAAGAACCACGTCCTGAGAAAC

CTAATGGAGATGAGAGGCCAACCAATGCTAAGGAAAATCAGGATGACAATTGCTCAGAAGTATTTAC

CCTTCTCCAAGAAGCTCATTGTTCCTCTGTAGCTTCAGTCAACAAAAATTGTGTACCAGCACTAGAG

GTTCTCAAAAAGACTAGCTCTTTCAGGGAGTTTGTACCTTCACCGAAGAAGGGAAATCATGATGCAT

GCAATGAATCCTTTATCACTGTCGAGCATGAAGCAAATCAAAAGTTGGACAGCTCTGATGCCAATCA

GACAGTTTTGGATAATGGCACTGTTAAACCTTCAAAATCAGAAAATTCTTGCTCTTTGCATGAGATA

TTGTTTCAGCAAAAGAAATCAGATGATTTTATTGGATCATTGCCAACAGATGAGATGAAAGCCATGC

AGAACTATCCAAGGCATGTCCCTGTACACGTTCTAGATGGGAGCCTGGGAACATGTATGGAAACTCC

CTCGGATTTGTCATTTCAGGATTCCATGTTTCATCCAGTAGGAGATATTCCAGCGTGTCCTATTTTA

TACTCACATCCTACTGGATCCACTACCACTGATCATCCAACTAATTTGCCAAGATCCTCTATGCATC

AATCATTTCCATTTTTTCCTCCTCCATTTACCCCAACTCATCATAATCAAGATGACTACAGATCATT

TCTCCACATATCCTCCACATTTTCGAGTCCCGTTGTATCTACTCTGCTACAAAACCCGGCAGCCCAT

GCTGCAGCAAGCTTTGCAGCTACCTTTTGGCCCTATGGAAATGTGGAGAGTTCCGCAGATTCTCCAG

CATGTGCCCAAGAAGGTTTCCAATCGGGGCAAATAAACTCTGCTCCCAGTATGGCAGCTATTGCTGC

TGCTACAGTGGCAGCAGCAACTGCATGGTGGGCAGCACATGGACTACTTCCCATATGTGCTCCTCTT

CACACTGCCTTTGCCTGCCCTCCTGCTTCTGCAACTGCAATTCAGTCTGCGGATACTGATCAAGTTC

CTCCAGCCAAGCCAGAAAGGAAGGAAACAACTCCTGATAATCCTCCTTTGCAAGGTCAAATACAGGA

CCTGGAGCACTCTGAAGCTGTGCAAGCTCAAAACTCTGCATCAAAACCACCAACGTTGTCATCATCA
```

```
GATTCTGAAGAGAGTGGAGGCACAAAGCTAAACACTGCACCAAAAGTTACTGATCACGAGTTAAATT

CAAAAGCTCCTGAGGTCCAGGATTCAGGCAAAACAAAGAGCAGAAAACAGGTTGACCGTTCTTCATG

TGGTTCAAATACACCATCTAGCAGTGAAATTGAGACAGATGCATTAGAGAAGAATGAGAAAGGCAAG

GAAGAGCCAAAAGAAGCTGATGCAAATCATCCAGCCTCTGAGTTGAACTGTCGCCGCAGCAGAAGTA

GCAGCAGCATGAGTGATTCGTGGAAAGAGGTCTCCGAAGAGGGGCGGCTGGCATTTCAAGCACTATT

CACCAGAGAGAGATTGCCCCAGAGCTTCTCACCTCCACATGATCTGAAGAGTAAGATGCACCAGAAG

GAAGATACTGAAGAAAAGAAAAATCCAGATGAGAAAGATGGAGATGCGTCACTGTTAGATCTCAACA

GCAAAACATGGGGTTACTGCTCTGGCTATCAAGAAGGGGAGAAAAATGCTGTAGTGCCTAGATGTGT

AAACGATGGGGAGGAAGGGCTGCTGACTATTGGACTTGGACATGGAAATCTGAAGGCTCATCTAACC

GGATTTAAACCTTACAAAAGGTGTTCACTGGAGGCCAAAGAAAGCAGGATGGGAACCACTGGTGGCC

AGGGCGAGGAGAAAGGCCCCAAGAGGTTACGTTTGGAAAGGGAAGCTTCAGTTTGATACTTGATACT

GCATGCTTAAACAAGGGAAAACCTTTGTTTTGTATGTAATTTCTAATTTTCTCCCTTGTCTATCAT

TCCGTTCATGTTTAAATTAGAGGAACGGCAACCCAGGAGACTTTTCGTGTAAGTGTGTGCTTATA

TATCAGACATTGGCTTATTTACTTTCTTGAACCCATGACTGCAGTTAAGTATCCATCAAAAGACCTA

GATAAGAACTTAAGAAGCATTAAGTATTGAATTG
```

The amino acid sequence of the polypeptide LHY1, in poplar plants, is referred to herein as SEQ ID NO.2, as follows:

```
                                                              [SEQ ID NO. 2]
MDTYSAGEDLVIKTRKPYTITKQRERWTEEEHNRFLEALKLYCRAWQRIEEHIGTKTAVQIRSHAQKFES

KLEKEAVAKGVPIGQALEIDIPPPRPKRKPSNPYPRKTGVGPPASQAGAKDGKLLTSTSSPHCRKVLDLE

KEPRPEKPNGDERPTNAKENQDDNCSEVFTLLQEAHCSSVASVNKNCVPALEVLKKTSSFREFVPSPKKG

NDDACNESFITVEHEANQKLDSSDANQTVLDNGTVKASKSENSCSLHEILFQQKSDDFIGSLPTDEMQA

MQNYPRHVPVHVLDGSLGTCIETPSDLSFQDSMFHPVGDIPACPILYSHPAGSTTTDHPTNLPRSSMHQS

FPFEPPPFTPTHHNQDDYRSELHISSTFSSPVVSTLLQNPAAHAAASFAATEMPYGNVESSADSPACAQE

GFQSGQINSAPSMAATAAATVAAATAWWAAHGLLPICAPLHIAEACPPASATAIQSADTDQVPPAKPERK

ETTPDNPPLQGQIQDLEHSEAVQAQNSASKPPTLSSSDSEESGGTKLNTGPKVTDDELNSKAPEVQDSGK

TKSRKQVDRSSCGSNTPSSSEIETDALEKTEKGKEEPKEADANHPASESNCRRSRSSSSMSDSWKEVSEE

GRLAFQALFTREILPQSFSPPHDLKSKMHQKEDTEEKKNPDEKDGDASLLDLNSKTWGYCSGYQEGEKNA

VVPRCVNDGEEGLLTIGLGHGNLKAHLTGEKPYKRCSLEAKESRMATTGGQGEEKGPKRLRLEREASV
```

In another embodiment, the core circadian clock gene may be Late Elongated Hypocotyl 2 (LHY2). The cDNA sequence encoding the polypeptide, LHY2, in poplar plants, is 2717 base pairs long, and is referred to herein as SEQ ID NO.3, as follows.

```
                                                              [SEQ ID NO. 3]
TTTCTCTTGGGAAGGAATTGGAGTCCATGCGTTCGTTTTGTTGTAGCGGAACGACGGCTTTATTTGTAGT

ATTGAGTGTTGCAAGAAATGAAGGGAGATTTCTTTTTTATCCCTTGCTCGTTAGAGAGGATTTGAAGCAG

CGTTGGCTGCCTAAGGTCCACTAATGGAAATATTCTCTTCTGGGGAAGACTTGGTTATTAAGACAAGGAA

ACCATATACAATTACCAAGCAACGAGAAAGATGGACAGAGGAGGAGCATAGCAGGTTCCTAGAGGCCTTG

AAGCTCTATGGACGAGCTTGGCAGCGAATTGAAGAACATATTGGTACAAAGACTGTCGTTCAGATCAGAA
```

-continued

```
GTCATGCACAGAAGTTCTTTTCAAAGTTGGAGAAGGAGGCTGTTGTTAAAGGTGTTCCAATAGGACAAGC
ACTTGACATTGACATTCCACCACCACGTCCCAAAAGGAAACCAAGCAATCCTTATCCTCGAAAGATAGGC
GTGGGTCCTCCCGCATCACAGGTGGGAGCAAAGGATGGAAAGCTTTTAACTTCAGCTTCTTTTCCGTGTT
GTAAGCAGGTTTTAGGCTTGGAGAAAGAACCACTTCCTGAGAAACTTAATGGAGATGAGAGGCCAACCAA
TGCTAAGGAAAATCAGGATGACAATTGCTCAGAAGTATTTTCCCTTCTCCAAGAACCTCACTGTTCTTCT
GTACCTTCAATCAACAAGAATTCTGTACCAACACTAGATATTCTCAAAAAGGCTAGCCCTTTCAGGGAGT
TCGTATCTTCACCGAAGGAGGGAAATCATGATCCAAGTAATCAATCCTCTGTCACCGTCGAGCTTGGAGC
AAATCAAAAGTTGGACAACTCTGATGTCAAACAGGATAACAGCACTAGTGAGTTTTCAAAATCAGAAAAC
TTTTGCTCTTTTTCTGAGAAATTGTTTCAGCAAAAGAAATCAGATGATTTTATTGGAGCATTGCGAACAG
ATGGGATGCAAGCCATGCAGAACTATCCAAGGCATGTCCCTGTGCATGTTCTAGATGGGAGCCTGGGAAC
ATGTATGCAAACTCCTCCCTCAGATTTTTCGTTTCAGGAATCCATGTTTCATCCAATAGGAGAAATTCCA
GCATGTCCTAATTTATATTCACATCCTGCTGCATCCAAAACCACTGATCATCCAAATATTTCACCGAGAT
CCTCTATGCATCAATCATTTCCAAGTTTTCCTCCTCCCTTTACCCCAACTCATCATAATCAAGATGACTA
CAGATCTTTCCTCCACATATCCTCCACATTTTCAAGCCTCGTTGTATCTTCTGCTACAAAACCCGGCA
GCCCATGCTGCAGCAAGCTTTGCATCTACCTTTTGGCCCTATGGAAATGTGGAGAGTTCTGCGGATTCTC
CAGCATGTGCCCAAGGAGGTTTCCAATCCAGGCAATTGAACTCTGCTCCTAGTATGGCAGCTATTGTTGC
TGCTACAGTGGCAGCAGCAACCGCATGGTGGACAGCGCATGGACTACTTCCCATGTGTGCCCCTCTTCAT
ACCTCGTTTGCCTGCCCTCCTGCATCTGCAACTGCAATTCAGTCTGAAAGAGCTGAAAATCCTTCTTTGC
AGGGACAAATACAGGGCCCAGAGCACACTGAAGCATTGCAAGCTCAAAACTCAGCATCTAAATCACCAAA
GATAACATCATCAGACTCTGAAGAGAGCGGAGGCCCAAAGCTAAATACTGGACCAGAAGTTATTGATCAT
GAGTTGACTACAAAACCTCACGAGGTCCAGGATTCAAGCAAAACAAAGAGCAGAAAACTGATTGACCGTT
CTTCATGTGGTTCAAACACACCTTCTAGCAGTGAAATAGAGACAGATGCATTAGAGAAGGCTGAGAAAGG
CACGGAAGAGCCAAAAGAAGATGATGCAAATCATCCAGCTTCCGAATCTAGCTCTCGCCACAGCAGAAGC
AGTAGCAGCATGAATGATTCATGGAAAGAGGTCTCCGAAGAGGGCGGCTGGCATTTCAAGCACTCTTCG
CTAGAGAGGTATTGCCCCAGAGCTTCTCACCTCCACATGATCTGAAGAGTAAGATGCACCAGAATGAAGA
TGCTGGAGAAAAGAAAGATGCAGATGAGAAAGATGGAGATGCATCACTGATAAATCTCAACAGTAAAACG
TGGGAGTGCTGCTCTGGTCATCAAGAAGGGGAGAAAAATGCTTTGTCTAGATGTGAAAACTATGGGGAGG
AGGAGCTGCTGACGATTGGGCTTGGACATGGAAAGCTTAAGGTTCGTCGAACCGGATTTAAACCTTACAA
AAGGTGTTCACTGGAGGCCAAAGAAAGCAGGACCGGAACCGGCAGCGGCCAGGGCGAGGAGAAAGGCCCC
AAGAGGTTACGTTTGGAAGGAGAAGCTTCAGTTTGATACTTGATATTGCTTGCTTGAATAAGGGAAAACC
TTTGTTTTTGCATGTAATTTATAATATCCTCGCTTGCCTATCATTCCTTTTATGTTTAAATTAGAGTATC
TGCAACCCACAAGACTTGTCGTGTAAGTGTGTGTACTATATGTCGACATTGGCTTATTTACTTTCTTGAA
CCCATTACCGCATTTAAGAACTCCGTTAAATAGACGTAGATAAGAACTTAAGAACCATTAGAACCATTAA
GTATTGAATTGGCTTTCCACGGCCCTTTTCCTCCAAAGTTCATAATTATTTTCTAAC
```

Accordingly, the amino acid sequence of the polypeptide LHY2, in poplar plants, is referred to herein as SEQ ID NO.4, as follows:

[SEQ ID NO. 4]
MEIFSSGEDLVIKTRKPYTITKQRERWTDEEHSRFLEALKLYGRAWQRIEEHIGTKTVVQIRSHAQKFFS

KLEKEAIVKGVPIGQALDIDIPPPRPKRKPSNPYPRKIGVGPPASQVGAKDGKLLTSASFPCCKQVLGLE

KEPLPEKLNGNERPTDAKENQDDNCSEVFSLLQEPHCSSVPSVNKNSVPTILTLKKASPFREFVSSPKEG

-continued

```
NHDASNQSSVTVDLGANQKLDNSDVKQDNSTSEFSKSENFCSFSEKLFQQKKSDDFIGALRTDGMQAMQN

YPRHVPVHVLDGSLGTCMQTPPSDFSFQESIFHPIGEIPACPNLYSHPAASKTTDHPNISPRSSMHQSFP

SFPPPFTPTHHNQDDYRSFLHMSSTFSSLVVSSLLQNPAAHAAASFASTFWPYGNVESSADSPACAQGGF

QSRQLNSAPSMAAIVAATVAAATAWWTAHGLLPMCAPLHTSFACPPASATAIQSVDTGQVSATKTERKET

AENPSLQGQIQDQEHTFALQAQNSASKSPKITSSDSEESGGPQLNTRPEVIDHELTTKPHEVQDSSKTKS

RKLIDRSSCGSNTPSSSEIETDALEKAEKGTEEPKEDDANHPASESSSRHSRSSSSMNDSWKEVSEEGRL

AFQTLFAREVLPQSFSPPHDLKSKMHQNEDAGEKKDADEKDGDASLINLNTKTWECCSGHQEGEKNALSR

CENYGEEGLLTIGLCHGKIKVRRTGFKPYKRCSLEAKESRTGTGSGQGEEKGPKRLRLEGEASV
```

Thus, the core circadian clock gene may comprise a nucleotide sequence substantially as set out in SEQ ID No.1 or 3, or a functional variant or fragment or orthologue thereof. The polypeptide encoded by the core circadian clock gene may comprise an amino acid sequence substantially as set out in SEQ ID No.2 or 4, or a functional variant or fragment or orthologue thereof.

In an alternative embodiment, the method may comprise modulating the concentration and/or activity of polypeptides encoded by the LHY1 and LHY2 genes, preferably simultaneously.

In another embodiment, the method may comprise increasing the density of lignin in the test plant. Advantageously, increasing plant lignin density is useful where lignin is harvested from plants as a source of energy, since the higher the density of lignin in a harvested plant, the better. Increasing lignin density may be achieved by decreasing the concentration and/or activity of the polypeptide encoded by the core circadian clock gene, which may be achieved by:—
(i) decreasing, preventing or attenuating transcription, translation or expression of the core circadian clock gene;
(ii) inhibiting synthesis of the polypeptide encoded by a core circadian clock gene, or its release from intracellular stores; or
(iii) increasing the rate of degradation of the polypeptide encoded by a core circadian clock gene.

In one embodiment, the method may comprise decreasing the concentration of the polypeptide encoded by the core circadian clock gene using RNAi. Therefore, the method may comprise transforming a cell of the test plant with an RNAi molecule, which is capable of down-regulating the expression of the core circadian clock gene. The method may comprise regenerating the test plant from the transformed cell.

The RNAi molecule may be capable of decreasing, in the transformed plant, the concentration of the polypeptide encoded by the circadian core clock gene by at least 5%, 10%, 20%, 30%, 40%, 50% or more, compared to the concentration of the polypeptide in the wild-type plant, which has not been transformed with the RNAi molecule.

The RNAi molecule may comprise a small interfering RNA (siRNA) molecule, or a short hairpin loop (shRNA) molecule. As described in the Examples, the inventors have demonstrated the surprising efficacy of siRNA molecules, for use in increasing lignin density in plants.

The sequence of one embodiment of the RNAi molecule may be referred to herein as SEQ ID No.5, as follows. SEQ ID No.5 may be used to down-regulate LHY1 and/or LHY2. The underlined regions of the sequence are complementary to primers, according to SEQ ID Nos. 6 & 7, which were used to amplify SEQ ID No. 5.

[SEQ ID NO. 5]
```
ATGGAAATATTCTCTTCTGGGGAAGACTTGGTTATTAAGACAAGGAAAC

CATATACAATTACCAAGCAACGAGAAAGATGGACAGAGGAGGAGCATAG

CAGGTTCCTAGAGGCCTTGAAGCTCTATGGACGAGCTTGGCAGCGAATT

GAAGAACATATTGGTACAAAGACTGTCGTTCAGATCAGAAGTCATGCAC

AGAAGTTCTTTTCAAAGTTGGAGAAGGAGGCTGTTGTTAAAGGTGTTCC

AATAGGACAA
```

Thus, the RNAi molecule of the invention may comprise a nucleotide sequence substantially as set out in SEQ ID No.5, or a functional variant, or fragment thereof.

It will be appreciated that it would be relatively straightforward for the skilled person to modify the sequence of the RNAi molecule (e.g. SEQ ID No.5) to produce variants or fragments of the RNAi molecule, which would still function to down-regulate the expression of the core circadian clock gene, thereby decreasing the concentration of the encoded polypeptide, and increase lignin density. Functional variants and fragments of an RNAi molecule may be readily identified by using standard laboratory techniques to determine whether or not the level of mRNA encoded by the targeted circadian clock gene has been reduced to below the level of the corresponding core circadian clock gene mRNA in a corresponding wild-type plant cell, grown under the same conditions. An example of such a technique is polymerase chain reaction (PCR). The skilled technician would appreciate that the concentration of the polypeptide encoded by the core circadian clock gene may be measured directly in wild-type and transgenic plants, by using standard techniques, such as Enzyme-linked immunosorbent assays (ELISA), Fluorescence-activated cell sorting, Western blotting or Chromatin Immunoprecipitation (ChIP).

In an alternative embodiment, the concentration and/or activity of the polypeptide encoded by the core clock gene may be decreased by mutating the endogenous core circadian clock gene, in order to prevent or reduce its transcription, or to produce a non-functional or poorly functional mutant version of the polypeptide, such that lignin density is increased.

In another embodiment, the method may comprise transforming a cell of the test plant with a genetic construct, which comprises a nucleic acid encoding an exogenous core clock gene polypeptide, wherein expression of the exogenous core clock gene polypeptide reduces the concentration of the endogenous polypeptide below the concentration of the endogenous polypeptide present within the corresponding wild-type plant grown under the same conditions. The exogenous core clock gene may be placed under the control of a promoter, such as a constitutive promoter or an inducible promoter.

Thus, according to a second aspect of the invention, there is provided use of a genetic construct which is capable of modulating the concentration and/or activity of a polypeptide encoded by a core circadian clock gene, for modulating the density of lignin in a plant.

In one embodiment, the construct may be capable of negatively modulating the circadian clock polypeptide, and is used to increase lignin density. The genetic construct may comprise an RNAi molecule, which may comprise a small interfering RNA (siRNA) molecule, or a short hairpin loop (shRNA) molecule. Alternatively, the genetic construct may comprise a nucleic acid encoding an exogenous core clock gene polypeptide which is capable of reducing the expression of the endogenous polypeptide encoded by the endogenous core clock gene.

Thus, according to a third aspect of the invention, there is provided use of a genetic construct which is capable of decreasing the concentration and/or activity of a polypeptide encoded by a core circadian clock gene, for increasing the density of lignin in a plant transformed with the construct.

However, in another embodiment, the construct may be capable of positively modulating the circadian clock polypeptide, and can be used to decrease lignin density.

Hence, in another embodiment, the method may comprise decreasing the density of lignin in the test plant. Advantageously, decreasing plant lignin density is useful in plants, which can be smoked, such as tobacco, in order to improve the flavour or alter the level of toxicants of the inhaled smoke. Decreasing lignin density may be achieved by increasing the concentration and/or activity of the polypeptide encoded by the core circadian clock gene, which may be achieved by:—
  (i) increasing, promoting or augmenting transcription, translation or expression of the core circadian clock gene;
  (ii) increasing synthesis of the polypeptide encoded by a core circadian clock gene, or its release from intracellular stores; or
  (iii) decreasing the rate of degradation of the polypeptide encoded by a core circadian clock gene.

The method may comprise transforming a cell of the test plant with a genetic construct which encodes an exogenous core circadian clock gene, or which comprises a nucleotide sequence which encodes a protein which is capable of promoting or augmenting the endogenous core circadian clock gene. It will be appreciated that each of these options would result in an increased concentration of the polypeptide encoded by the core circadian clock gene. The method may comprise regenerating the test plant from the transformed cell.

The construct may be capable of increasing, in the transformed plant, the concentration of the polypeptide encoded by the circadian core clock gene by at least 5%, 10%, 20%, 30%, 40%, 50% or more, compared to the concentration of the polypeptide in the wild-type plant, which has not been transformed with the construct.

Thus, according to a fourth aspect of the invention, there is provided use of genetic construct which is capable of increasing the concentration and/or activity of a polypeptide encoded by a core circadian clock gene, for decreasing the density of lignin in a plant transformed with the construct.

The genetic construct may encode a polypeptide comprising the amino acid sequence substantially as set out in SEQ ID No's:2 or 4, or a functional variant or fragment or orthologue thereof. The construct may comprise the nucleotide sequence substantially as set out in either SEQ ID No: 1 or 3, or a functional variant or fragment or orthologue thereof.

Genetic constructs of the invention may be in the form of an expression cassette, which may be suitable for expression of the core circadian clock gene in a host cell. The RNAi molecule or genetic construct may be introduced into a host cell without it being incorporated in a vector. For instance, the RNAi molecule or genetic construct, which may be a nucleic acid molecule, may be incorporated within a liposome or a virus particle. Alternatively, a purified nucleic acid molecule (e.g. histone-free DNA or naked DNA) may be inserted directly into a host cell by suitable means, e.g. direct endocytotic uptake. The genetic construct may be introduced directly in to cells of a host subject (e.g. a plant) by transfection, infection, microinjection, cell fusion, protoplast fusion or ballistic bombardment. Alternatively, genetic constructs of the invention may be introduced directly into a host cell using a particle gun.

Alternatively, the genetic construct may comprise or be harboured within a recombinant vector, for expression in a suitable host cell. The recombinant vector may be a plasmid, cosmid or phage. Such recombinant vectors are highly useful for transforming host cells with the genetic construct of the invention, and for replicating the expression cassette therein. The skilled technician will appreciate that genetic constructs of the invention may be combined with many types of backbone vector for expression purposes. The backbone vector may be a binary vector, for example one which can replicate in both *E. coli* and *Agrobacterium tumefaciens*. For example, a suitable vector may be a pBIN plasmid, such as pBIN19 (Bevan M., 1984, Nucleic Acids Research 12:8711-21).

Recombinant vectors may include a variety of other functional elements in addition to the coding sequence of the core circadian clock gene. For example, the vector may comprise a promoter. In addition, the recombinant vector may be designed such that it autonomously replicates in the cytosol of the host cell. In this case, elements which induce or regulate DNA replication may be required in the recombinant vector. Alternatively, the recombinant vector may be designed such that it integrates into the genome of a host cell. In this case, DNA sequences which favour targeted integration (e.g. by homologous recombination) are envisaged.

The recombinant vector may also comprise DNA coding for a gene that may be used as a selectable marker in the cloning process, i.e. to enable selection of cells that have been transfected or transformed, and to enable the selection of cells harbouring vectors incorporating heterologous DNA. The vector may also comprise DNA involved with regulating expression of the coding sequence, or for targeting the expressed polypeptide to a certain part of the host cell, e.g. the chloroplast. Hence, the vector may comprise at least one additional element selected from a group consisting of: a selectable marker gene (e.g. an antibiotic resistance gene); a polypeptide termination signal; and a protein targeting sequence (e.g. a chloroplast transit peptide).

Examples of suitable marker genes include antibiotic resistance genes such as those conferring resistance to Kanamycin, Geneticin (G418) and Hygromycin (npt-II, hyg-B); herbicide resistance genes, such as those conferring resistance to phosphinothricin and sulphonamide based herbicides (bar and suI respectively; EP-A-242246, EP-A-0249637); and screenable markers such as beta-glucuronidase (GB2197653), luciferase and green fluorescent protein (GFP). The marker gene may be controlled by a second promoter, which allows expression in cells, which may or may not be in the seed, thereby allowing the selection of cells or tissue containing the marker at any stage of development of the plant. Suitable second promoters are the promoter of nopaline synthase gene of *Agrobacterium* and the promoter derived from the gene which encodes the 35S cauliflower mosaic virus (CaMV) transcript. However, any other suitable second promoter may be used.

The various embodiments of genetic constructs of the invention may be prepared using the following cloning procedure. The genomic or cDNA versions of a circadian clock gene to be expressed in the test plant may be amplified from the genomic or cDNA templates by PCR using suitable primers, for example SEQ ID No's 6 and 7, as described in the Examples. PCR products may then be examined using agarose gel electrophoresis. The PCR products may then be ligated into a suitable vector for cloning purposes, for example the pCR4 Blunt-TOPO vector (Invitrogen). Vectors harbouring the PCR products may be grown up in a suitable host, such as *E. coli*. *E. coli* colonies may then be screened by PCR using suitable primers, and inserts in plasmids showing the correct restriction enzyme digest pattern may be sequenced using suitable primers.

*E. coli* colonies carrying the construct may be cultured to produce a suitable amount of each plasmid, which may then be purified. The plasmids may then be digested to release a DNA fragment corresponding to the core circadian clock gene, which may then be cloned into a vector harbouring a suitable promoter, for example either the CERV or pea plastocyanin (PPC) promoter, such as a pBNP plasmid (van Engelen et al., 1995, Transgenic Research, 4: 288-290).

In view of their surprising results, the inventors believe that they are the first to have developed a method for producing a transgenic plant in which the lignin density can be modulated by careful manipulation of the plant's circadian rhythm.

Thus, in a fifth aspect of the invention, there is provided a method of producing a transgenic plant in which the density of lignin is modulated compared to the corresponding lignin density in a wild-type plant cultured under the same conditions, the method comprising the steps of:—
(i) transforming a plant cell with a genetic construct which is capable of modulating the concentration and/or activity of a polypeptide encoded by a core circadian clock gene; and
(ii) regenerating a plant from the transformed plant cell.

Furthermore, in a sixth aspect, there is provided a method for producing a transgenic plant, the method comprising introducing, into an unmodified plant, an exogenous core circadian clock gene, wherein expression of the core circadian clock decreases lignin density in the transgenic plant relative to the density of lignin in the unmodified plant.

In a seventh aspect, there is provided a transgenic plant obtained or obtainable from the method of the fifth and sixth aspect, wherein the transgenic plant comprises a modulated lignin concentration compared to a wild-type plant cultured under the same conditions.

In an eighth aspect, there is provided use of an exogenous core circadian clock gene for reducing lignin density in a plant by transformation of the plant with the exogenous gene.

The term "unmodified plant" can mean a plant before transformation with an exogenous gene or a construct of the invention. The unmodified plant may therefore be a wild-type plant.

The term "exogenous gene" can mean the gene that is transformed into the unmodified plant is from an external source, i.e. from a different species to the one being transformed. The exogenous core circadian clock gene may comprise a nucleic acid sequence substantially the same or different to an endogenous core circadian clock gene in the unmodified plant. The exogenous gene may be derived from a genomic or cDNA sequence corresponding to the core circadian clock gene from any species, such as the Poplar genes, LHY1 or LHY2. The exogenous gene may form a chimeric gene. The exogenous gene may encode a polypeptide comprising the amino acid sequence substantially as set out in SEQ ID No's:2 or 4, or a functional variant or fragment or orthologue thereof. The exogenous gene may comprise the nucleotide sequence substantially as set out in either SEQ ID No: 1 or 3, or a functional variant or fragment or orthologue thereof.

The methods and uses of the invention may comprise transforming a test plant cell or unmodified plant cell with a genetic construct or the exogenous gene described herein. For example, the construct may be an RNAi molecule, preferably an siRNA molecule.

In a ninth aspect, there is provided a plant host cell comprising a genetic construct which is capable of modulating the concentration and/or activity of a polypeptide encoded by a core circadian clock gene.

The plant host cell may be used for modulating the density of lignin in a plant comprising the plant host cell.

Thus, in a tenth aspect, there is provided use of a plant host cell comprising a genetic construct which is capable of modulating the concentration and/or activity of a polypeptide encoded by a core circadian clock gene, for modulating the density of lignin in a plant comprising the plant host cell.

The cell may be a plant cell. The cell may be transformed with genetic constructs, vectors or exogenous genes according to the invention, using known techniques. Suitable means for introducing the genetic construct into the host cell may include use of a disarmed Ti-plasmid vector carried by *Agrobacterium* by procedures known in the art, for example as described in EP-A-0116718 and EP-A-0270822. A further method may be to transform a plant protoplast, which involves first removing the cell wall and introducing the nucleic acid, and then reforming the cell wall. The transformed cell may then be grown into a plant.

Preferably, and advantageously, the methods and uses according to the invention do not compromise the health or fitness of the test or transgenic plant that is generated. The transgenic or test plants according to invention may include the Brassicaceae family, such as *Brassica* spp. The plant may be *Brassica napus* (oilseed rape). Further examples of transgenic or test plants include the family Poales, such as *Triticeae* spp. The plant may be *Triticum* spp. (wheat). The plant may or may not be Poplar, i.e. of the *Populus* genus.

Further examples of suitable transgenic or test plants according to the invention may include the Solanaceae family of plants which include, for example jimson weed, eggplant, mandrake, deadly nightshade (belladonna), capsicum (paprika, chili pepper), potato and tobacco. One example of a suitable genus of Solanaceae is *Nicotiana*. A suitable species of *Nicotiana* may be referred to as tobacco plant, or simply tobacco.

Other examples of suitable transgenic or test plants according to the invention may include Sugarcane or the Salicaceae family of plants, for Example Aspen or cottonwoods. Further examples of transgenic or test plants include the Poaceae family of plants, for example *Panicum virgatum* (Switch Grass), *Hordeum vulgare* L. (Barley) or *Miscanthus*.

Tobacco may be transformed with constructs, vectors and exogenous genes of the invention as follows.

*Nicotiana tabacum* is transformed using the method of leaf disk co-cultivation essentially as described by Horsch et al. 1985 (Science, 227: 1229-1231). The youngest two expanded leaves may be taken from 7-week old tobacco plants and may be surface-sterilised in 8% Domestos™ for 10 minutes and washed 6 times with sterile distilled water. Leaf disks may be cut using a number 6 cork borer and placed in the *Agrobacterium* suspension, containing the appropriate binary vectors (according to the invention), for approximately two minutes. The discs may be gently blotted between two sheets of sterile filter paper. Ten disks may be placed on LS media+3% sucrose+2 µM BAP+0.2 µM NAA plates, which may then be incubated for 2 days in the growth room. Discs may be transferred to plates of LS media+3% sucrose+2 µM BAP+0.2 µM NAA supplemented with 500 g/l claforan and 100 g/l kanamycin. The discs may be transferred onto fresh plates of above medium after 2 weeks. After a further two weeks, the leaf disks may be transferred onto plates containing LS media+3% sucrose+0.5 µM BAP supplemented with 500 mg/l claforan and 100 mg/l kanamycin. The leaf disks may be transferred onto fresh medium every two weeks. As shoots appear, they may be excised and transferred to jars of LS media+3% sucrose supplemented with 500 mg/l claforan. The shoots in jars may be transferred to LS media+3% sucrose+250 mg/l claforan after approximately 4 weeks. After a further 3-4 weeks the plants may be transferred to LS media+3% sucrose (no antibiotics) and rooted. Once the plants are rooted they may be transferred to soil in the greenhouse.

In an eleventh aspect, there is provided a plant propagation product comprising a genetic construct which is capable of modulating the concentration and/or activity of a polypeptide encoded by a core circadian clock gene.

The propagation product may be used for modulating the density of lignin in a plant derived from the plant propagation product.

Hence, in a twelfth aspect, there is provided use of a plant propagation product comprising a genetic construct which is capable of modulating the concentration and/or activity of a polypeptide encoded by a core circadian clock gene, for modulating the density of lignin in a plant derived from the plant propagation product.

A "plant propagation product" may be any plant matter taken from a plant from which further plants may be produced. Suitably, the plant propagation product may be a seed. The plant propagation product may preferably comprise a genetic construct, vector or exogenous gene according to the invention.

The inventors have observed that a test plant (i.e. a transgenic plant) which has been transformed with an RNAi molecule according to the invention exhibits a surprising increase in lignin density. As such, this embodiment of the transgenic plant exhibits profound utility as an energy source.

Accordingly, in a thirteenth aspect, there is provided use of a transgenic plant comprising a genetic construct which is capable of modulating the concentration and/or activity of a polypeptide encoded by a core circadian clock gene, as a lignin fuel source.

Preferably, the construct is capable of decreasing the concentration and/or activity of the polypeptide encoded by the core circadian clock gene, such that the density of the lignin in the plant increases.

The inventors have also observed that a test plant (i.e. a transgenic plant) which has been transformed with a construct which increases the concentration and/or activity of the polypeptide encoded by the core circadian clock gene exhibits a decrease in lignin density. Accordingly, this embodiment of the transgenic plant is extremely useful in improving the flavour or toxicant level in smoking tobacco, for example.

Thus, in a fourteenth aspect, there is provided use of a transgenic plant comprising a genetic construct which is capable of modulating the concentration and/or activity of a polypeptide encoded by a core circadian clock gene, for improving the flavour of tobacco.

Also, in a fifteenth aspect, there is provided a harvested leaf having a lower density of lignin than the corresponding density of lignin in a harvested leaf taken from a wild-type plant cultured under the same conditions, wherein the leaf is harvested from a transgenic plant comprising a genetic construct which is capable of increasing the concentration and/or activity of a polypeptide encoded by a core circadian clock gene.

In a sixteenth aspect, there is provided a tobacco product comprising lignin-reduced tobacco obtained from a mutant tobacco plant, which mutant is capable of decreasing the density of lignin in its leaves by increasing the concentration and/or activity of a polypeptide encoded by a core circadian clock gene.

It is preferred that the mutant tobacco plant from which the tobacco in the tobacco product is derived comprises a construct, vector or exogenous gene according to the invention. For example, the construct may comprise an exogenous LHY1 or LHY2 gene.

The tobacco product may be smokeless tobacco product, such as snuff. The tobacco product may be an oral tobacco product deliverable by the mouth. The tobacco product may be moist, and may be snus. However, the tobacco product may also be a smoking article.

Thus, in a seventeenth aspect, there is provided a smoking article comprising lignin-reduced tobacco obtained from a mutant tobacco plant, which mutant is capable of decreasing the density of lignin in its leaves by increasing the concentration and/or activity of a polypeptide encoded by a core circadian clock gene.

Lignin-reduced tobacco can include tobacco in which the lignin concentration or density is less than the corresponding amount in a wild-type plant cultured under the same conditions. Such a smoking article may comprise tobacco obtained from a mutant tobacco plant, which may have been transformed with a genetic construct, vector or exogenous gene of the invention. Preferably, the mutant tobacco plant comprises the construct which increases the concentration and/or activity of the polypeptide encoded by the core circadian clock gene, such as LHY1 and/or LHY2.

The term "smoking article" can include smokeable products, such as rolling tobacco, cigarettes, cigars and cigarillos whether based on tobacco, tobacco derivatives, expanded tobacco, reconstituted tobacco or tobacco substitutes and also heat-not-burn products.

It will be appreciated that the invention extends to any nucleic acid or peptide or variant, derivative or analogue thereof, which comprises substantially the amino acid or nucleic acid sequences of any of the sequences referred to herein, including functional variants or functional fragments thereof. The terms "substantially the amino acid/polynucleotide/polypeptide sequence", "functional variant" and "functional fragment", can be a sequence that has at least 40% sequence identity with the amino acid/polynucleotide/polypeptide sequences of any one of the sequences referred to herein, for example 40% identity with the polynucleotide sequence identified as SEQ ID No.5 (which encodes one embodiment of an RNAi sequence targeted against the core clock gene LHY1 and/or LHY2), or 40% identity with the polypeptide identified as SEQ ID No.2 (i.e. one embodiment of the polypeptide LHY1).

Amino acid/polynucleotide/polypeptide sequences with a sequence identity which is greater than 65%, more preferably greater than 70%, even more preferably greater than 75%, and still more preferably greater than 80% sequence identity to any of the sequences referred to is also envisaged. Preferably, the amino acid/polynucleotide/polypeptide sequence has at least 85% identity with any of the sequences referred to, more preferably at least 90% identity, even more preferably at least 92% identity, even more preferably at least 95% identity, even more preferably at least 97% identity, even more preferably at least 98% identity and, most preferably at least 99% identity with any of the sequences referred to herein.

The skilled technician will appreciate how to calculate the percentage identity between two amino acid/polynucleotide/polypeptide sequences. In order to calculate the percentage identity between two amino acid/polynucleotide/polypeptide sequences, an alignment of the two sequences must first be prepared, followed by calculation of the sequence identity value. The percentage identity for two sequences may take different values depending on:—(i) the method used to align the sequences, for example, ClustalW, BLAST, FASTA, Smith-Waterman (implemented in different programs), or structural alignment from 3D comparison; and (ii) the parameters used by the alignment method, for example, local vs global alignment, the pair-score matrix used (e.g. BLOSUM62, PAM250, Gonnet etc.), and gap-penalty, e.g. functional form and constants.

Having made the alignment, there are many different ways of calculating percentage identity between the two sequences. For example, one may divide the number of identities by: (i) the length of shortest sequence; (ii) the length of alignment; (iii) the mean length of sequence; (iv) the number of non-gap positions; or (iv) the number of equivalenced positions excluding overhangs. Furthermore, it will be appreciated that percentage identity is also strongly length dependent. Therefore, the shorter a pair of sequences is, the higher the sequence identity one may expect to occur by chance.

Hence, it will be appreciated that the accurate alignment of protein or DNA sequences is a complex process. The popular multiple alignment program ClustalW (Thompson et al., 1994, Nucleic Acids Research, 22, 4673-4680; Thompson et al., 1997, Nucleic Acids Research, 24, 4876-4882) is a preferred way for generating multiple alignments of proteins or DNA in accordance with the invention. Suitable parameters for ClustalW may be as follows: For DNA alignments: Gap Open Penalty=15.0, Gap Extension Penalty=6.66, and Matrix=Identity. For protein alignments: Gap Open Penalty=10.0, Gap Extension Penalty=0.2, and Matrix=Gonnet. For DNA and Protein alignments: ENDGAP=−1, and GAPDIST=4. Those skilled in the art will be aware that it may be necessary to vary these and other parameters for optimal sequence alignment.

Preferably, calculation of percentage identities between two amino acid/polynucleotide/polypeptide sequences is then calculated from such an alignment as (N/T)*100, where N is the number of positions at which the sequences share an identical residue, and T is the total number of positions compared including gaps but excluding overhangs. Hence, a most preferred method for calculating percentage identity between two sequences comprises (i) preparing a sequence alignment using the ClustalW program using a suitable set of parameters, for example, as set out above; and (ii) inserting the values of N and T into the following formula:— Sequence Identity=(N/T)*100.

Alternative methods for identifying similar sequences will be known to those skilled in the art. For example, a substantially similar nucleotide sequence will be encoded by a sequence which hybridizes to the sequences shown in SEQ ID No's. 1 or 3, or their complements under stringent conditions. By stringent conditions, we mean the nucleotide hybridises to filter-bound DNA or RNA in 3× sodium chloride/sodium citrate (SSC) at approximately 45° C. followed by at least one wash in 0.2×SSC/0.1% SDS at approximately 20-65° C. Alternatively, a substantially similar polypeptide may differ by at least 1, but less than 5, 10, 20, 50 or 100 amino acids from the sequences shown in SEQ ID No's.2 or 4.

Due to the degeneracy of the genetic code, it is clear that any nucleic acid sequence could be varied or changed without substantially affecting the sequence of the protein encoded thereby, to provide a functional variant thereof. Suitable nucleotide variants are those having a sequence altered by the substitution of different codons that encode the same amino acid within the sequence, thus producing a silent change. Other suitable variants are those having homologous nucleotide sequences but comprising all, or portions of, sequence, which are altered by the substitution of different codons that encode an amino acid with a side chain of similar biophysical properties to the amino acid it substitutes, to produce a conservative change. For example small non-polar, hydrophobic amino acids include glycine, alanine, leucine, isoleucine, valine, proline, and methionine. Large non-polar, hydrophobic amino acids include phenylalanine, tryptophan and tyrosine. The polar neutral amino acids include serine, threonine, cysteine, asparagine and glutamine. The positively charged (basic) amino acids include lysine, arginine and histidine. The negatively charged (acidic) amino acids include aspartic acid and glutamic acid. It will therefore be appreciated which amino acids may be replaced with an amino acid having similar biophysical properties, and the skilled technician will know the nucleotide sequences encoding these amino acids.

All of the features described herein (including any accompanying claims, abstract and drawings), and/or all of the steps of any method or process so disclosed, may be combined with any of the above aspects in any combination, except combinations where at least some of such features and/or steps are mutually exclusive.

In order to address various issues and advance the art, the entirety of this disclosure shows by way of illustration various embodiments in which the claimed invention(s) may be practiced and provide for superior transgenic plants. The advantages and features of the disclosure are of a representative sample of embodiments only, and are not exhaustive and/or exclusive. They are presented only to assist in understanding and teach the claimed principles. It should be understood that they are not representative of all claimed inventions. As such, certain aspects of the disclosure have not been discussed herein. That alternate embodiments may not have been presented for a specific portion of the invention or that further undescribed alternate embodiments may be available for a portion is not to be considered a disclaimer of those alternate embodiments. It will be appreciated that many of those undescribed embodiments incorporate the same principles of the invention and others are equivalent. Thus, it is to be understood that other embodiments may be utilized and modifications may be made without departing from the scope and/or spirit of the disclosure. As such, all examples, implementations, and/or embodiments are deemed to be non-limiting throughout this disclosure. Also, no inference should be drawn regarding those embodiments discussed herein relative to those not discussed herein other than it is as such for purposes of reducing space and repetition.

Various embodiments may suitably comprise, consist of, or consist essentially of, various combinations of the disclosed elements, components, features, parts, steps, means, etc. Some of the disclosed features, elements, implementation, etc., may be mutually contradictory, in that they cannot be simultaneously present in a single embodiment. Similarly, some features are applicable to one aspect of the disclosure, and inapplicable to others. In addition, the disclosure includes other inventions not presently claimed. Applicant reserves all rights in those presently unclaimed inventions including the right to claim such inventions, file additional applications, continuations, continuations in part, divisions, and/or the like thereof. As such, it should be understood that advantages, embodiments, examples, function, features, structural, and/or other aspects of the disclosure are not to be considered limitations on the disclosure as defined by the claims or limitations on equivalents to the claims.

BRIEF DESCRIPTION OF DRAWINGS

For a better understanding of the invention, and to show how embodiments of the same may be carried into effect, reference will now be made, by way of example, to the accompanying Figures, in which:—

Figure 1A:
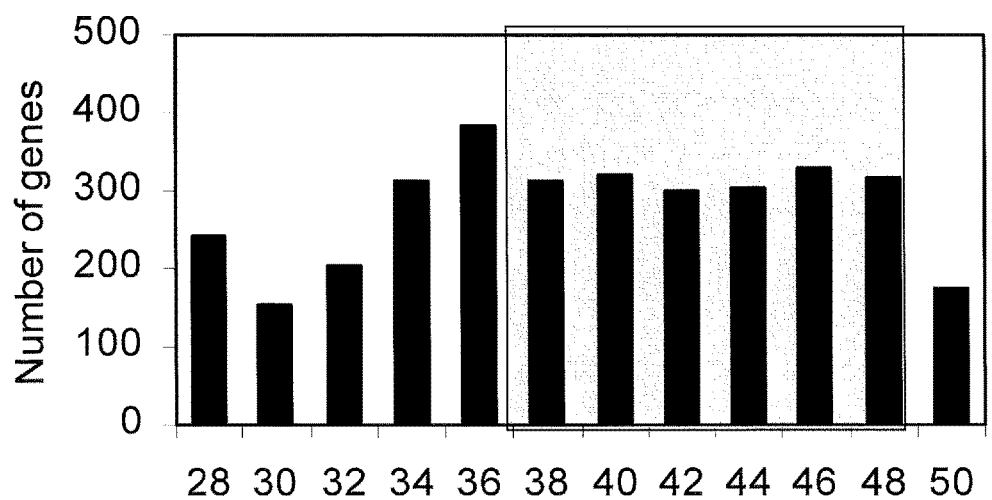
FIG. 1A shows a histogram of peak phase gene expression, of 9-10-day old *Arabidopsis* plants grown under cycles of 12-hour light and 12-hour dark cycles and transferred to constant light at dawn on day 8.

| Probe set | Group | Ortholog | Full gene name |
| --- | --- | --- | --- |
| PtpAffx.140781.1.A1_at | IPT | IPT3 | Isopentenyltransferase 3 |
| PtpAffx.204199.1.S1_at | IPT | IPT5 | Isopentenyltransferase 5 |
| PtpAffx.207604.1.S1_at | IPT | IPT5 | Isopentenyltransferase 5 |
| PtpAffx.208017.1.S1_at | IPT | IPT1 | Isopentenyltransferase 1 |
| PtpAffx.208947.1.S1_at | IPT | IPT1 | Isopentenyltransferase 1 |
| PtpAffx.36758.1.A1_at | IPT | IPT5 | Isopentenyltransferase 5 |
| PtpAffx.80325.1.S1_s_at | CYP735A | CYP735A1 | |
| PtpAffx.129568.2.A1_a_at | tRNA-IPT | tRNA-IPT9 | tRNAdimethylallyltransferase 9 |
| PtpAffx.204470.1.S1_at | tRNA-IPT | tRNA-IPT2 | tRNA dimethylallyltransferase 2 |

-continued

| Probe set | Group | Ortholog | Full gene name |
|---|---|---|---|
| Ptp.1999.2.S1_s_at | ADK | ADK2 | Adenosine Kinase 2 |
| PtpAffx.5888.1.A1_a_at | ADK | ADK2 | Adenosine Kinase 2 |
| PtpAffx.5888.1.A1_s_at | ADK | ADK2 | Adenosine Kinase 2 |
| PtpAffx.5888.4.A1_at | ADK | ADK2 | Adenosine Kinase 2 |
| PtpAffx.124853.1.S1_s_at | LOG | LOG_AT5G06300 | Lonely Guy |
| PtpAffx.14501.1.S1_at | LOG | LOG_AT2G28305 | Lonely Guy |
| PtpAffx.161404.1.S1_s_at | LOG | LOG_AT5G11950 | Lonely Guy |
| PtpAffx.200028.1.S1_at | LOG | LOG_AT5G11950 | Lonely Guy |
| PtpAffx.200028.1.S1_x_at | LOG | LOG_AT5G11950 | Lonely Guy |
| PtpAffx.203629.1.S1_at | LOG | LOG_AT5G11950 | Lonely Guy |
| PtpAffx.204340.1.S1_s_at | LOG | LOG_AT4G35190 | Lonely Guy |
| PtpAffx.204494.1.S1_at | LOG | LOG_AT4G35190 | Lonely Guy |
| PtpAffx.205060.1.S1_at | LOG | LOG_AT2G28305 | Lonely Guy |
| PtpAffx.205860.1.S1_at | LOG | LOG_AT4G35190 | Lonely Guy |
| PtpAffx.206667.1.S1_at | LOG | LOG_AT5G11950 | Lonely Guy |
| PtpAffx.57813.1.A1_at | LOG | LOG_AT4G35190 | Lonely Guy |
| PtpAffx.92499.1.S1_a_at | LOG | LOG_AT2G28305 | Lonely Guy |
| PtpAffx.112402.1.S1_at | TAR | TAR1_AT1G23320 | TRYPTOPHAN AMINOTRANSFERASE RELATED1 |
| PtpAffx.208683.1.S1_at | TAA | TAA1_AT1G70560 | TRYPTOPHAN AMINOTRANSFERASE of *ARABIDOPSIS* 1 |
| PtpAffx.210583.1.S1_at | TAR | TAR2_AT4G24670 | TRYPTOPHAN AMINOTRANSFERASE RELATED 2 |
| PtpAffx.213567.1.S1_at | TAR | TAR1_AT1G23320 | TRYPTOPHAN AMINOTRANSFERASE RELATED 1 |
| PtpAffx.54853.2.A1_at | TAR | TAR1_AT1G23320 | TRYPTOPHAN AMINOTRANSFERASE RELATED 1 |
| PtpAffx.203842.1.S1_at | CYP79B | CYP79B2_AT4G39950 | CYP79B2 |
| PtpAffx.54416.1.S1_at | CYP79B | CYP79B2_AT4G39950 | CYP79B2 |
| PtpAffx.82668.1.A1_at | CYP79B | CYP79B3_AT2G22330 | CYP79B3 |
| PtpAffx.202709.1.S1_at | YUC | YUC8 | YUCCA8 |
| PtpAffx.206743.1.S1_at | YUC | YUC6 | YUCCA6 |
| PtpAffx.206765.1.S1_at | YUC | YUC4 | YUCCA4 |
| PtpAffx.207340.1.S1_at | YUC | YUC6 | YUCCA6 |
| PtpAffx.208231.1.S1_at | YUC | YUC3 | YUCCA3 |
| PtpAffx.208604.1.S1_at | YUC | YUC3 | YUCCA3 |
| PtpAffx.212071.1.S1_at | YUC | YUC10 | YUCCA10 |
| PtpAffx.214153.1.S1_at | YUC | YUC6 | YUCCA6 |
| PtpAffx.214180.1.S1_at | YUC | YUC4 | YUCCA4 |
| PtpAffx.38860.1.S1_at | AMI | AMI1_AT1G08980 | AMIDASE 1 |
| PtpAffx.38860.2.S1_a_at | AMI | AMI1_AT1G08980 | AMIDASE 1; |

Figure 3A:
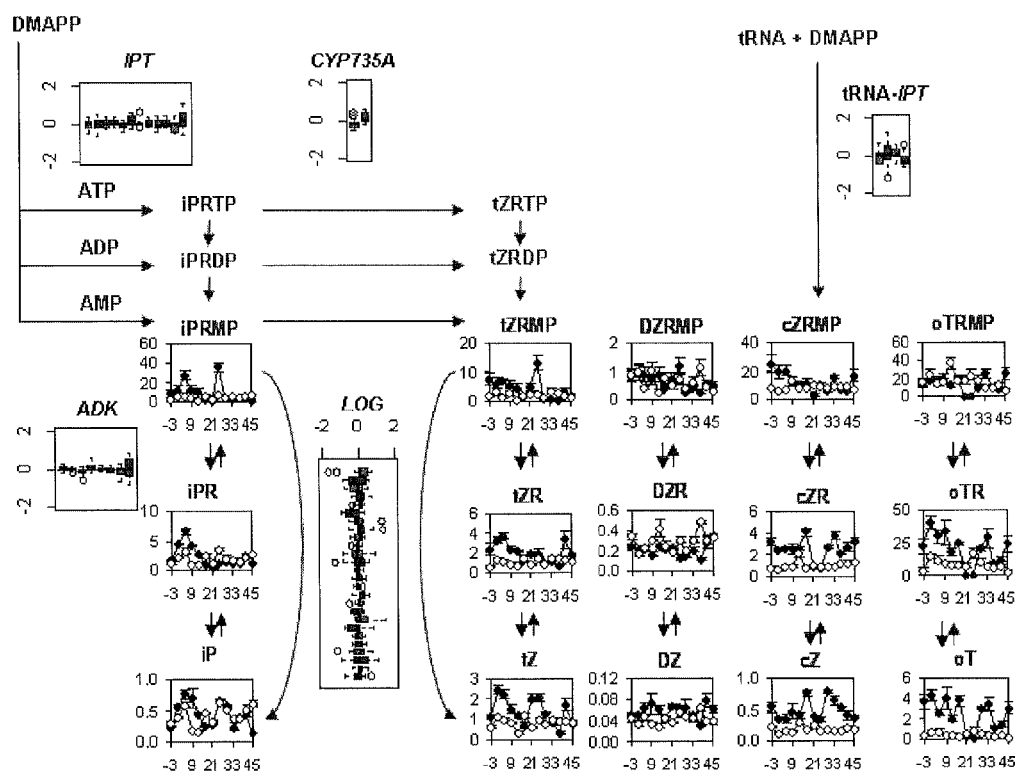
FIG. 3a shows the level of metabolites and gene expression for the cytokinin biosynthesis, metabolism and response pathway measured in wild type and lhy-10 Poplar trees. Arrows indicate the direction of flow for metabolites and regulation for transcripts. Metabolite (blue text) levels (pmoles/g F.W.) are shown over time (ZT hours) for wild type (black diamonds) and lhy-10 (open diamonds) plants. Error bars represent Standard deviation. A biological replicate consisting of four leaves such that two leaf blades from two independent individuals were collected at internode 8-11 and pooled (first internode defined as below a leaf with a blade at least 1 cm long) Cytokinin analysis was conducted with four technical replicates from a such biological pool. Transcript (Black text) levels shown as boxplots for each probe set representing Poplar orthologs of the genes across all time points. lhy-10 (red) and WT (blue) levels shown next to each other for each probe set on the *Populus trichocarpa* microarray in left to right order as listed in the table below.
Figure 3B:
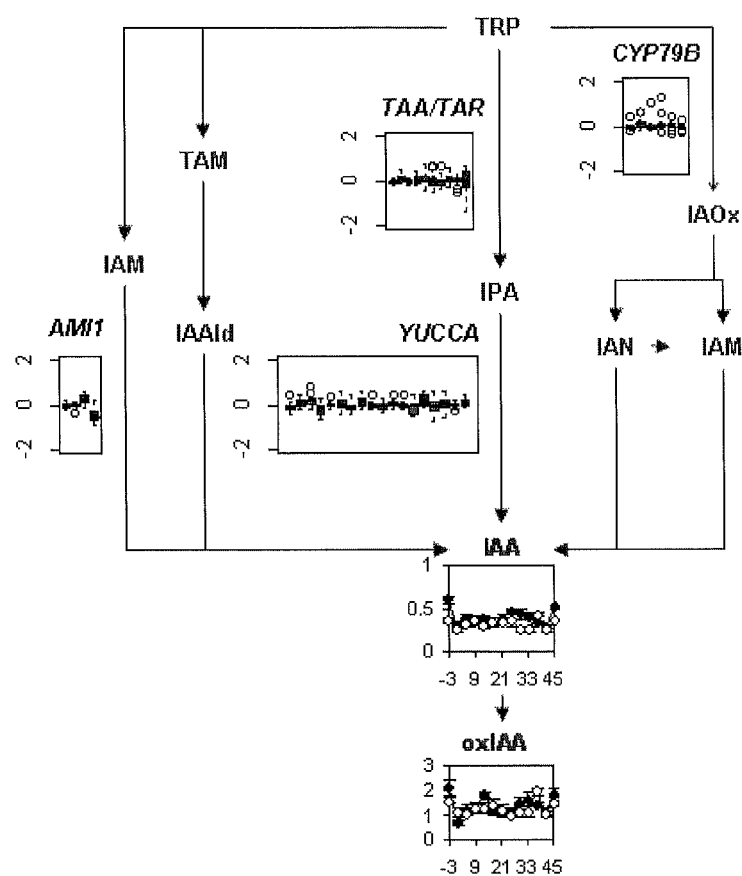
FIG. 3b shows metabolites and gene expression for the auxin biosynthesis, metabolism and response pathway measured in wild type and lhy-10 Poplar trees. Two biological pools (as above) were used for analysis, each with three technical replicates.
Figure 4B:
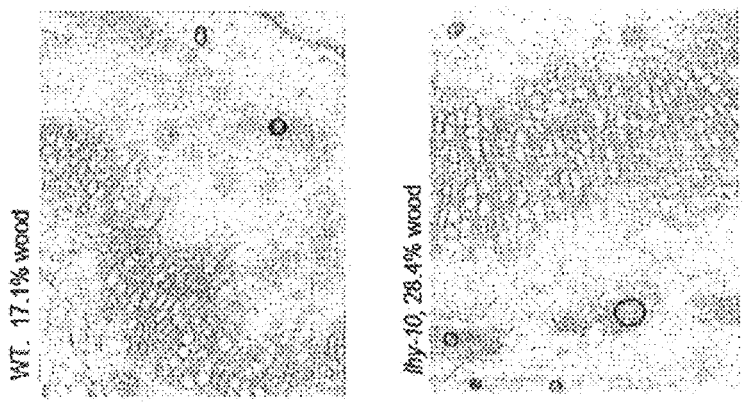
Figure 4A:
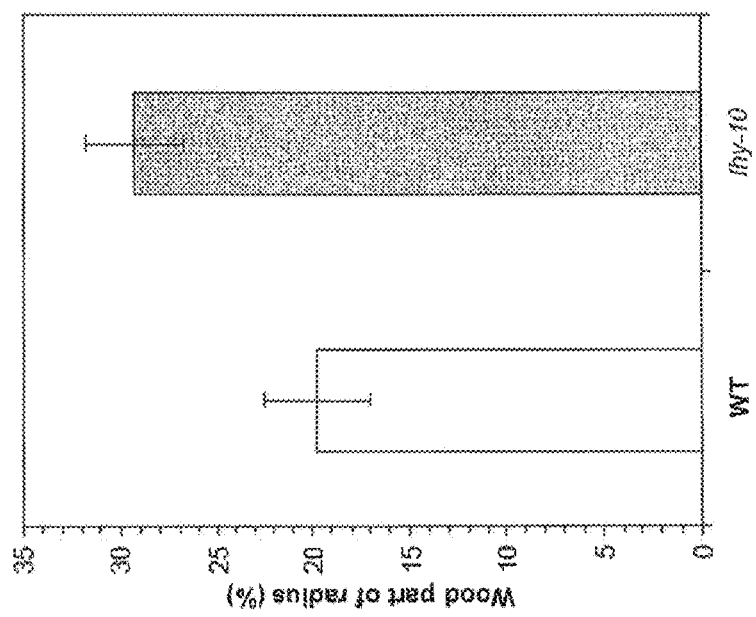
Figure 5A:
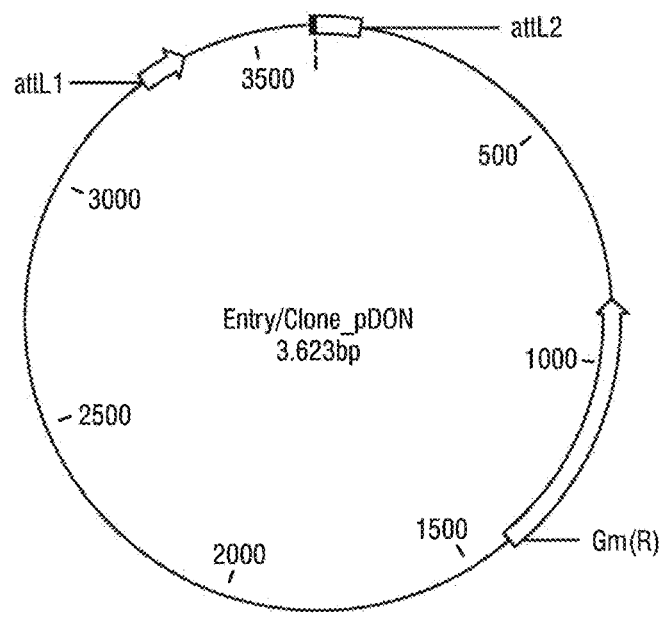
Figure 5B:
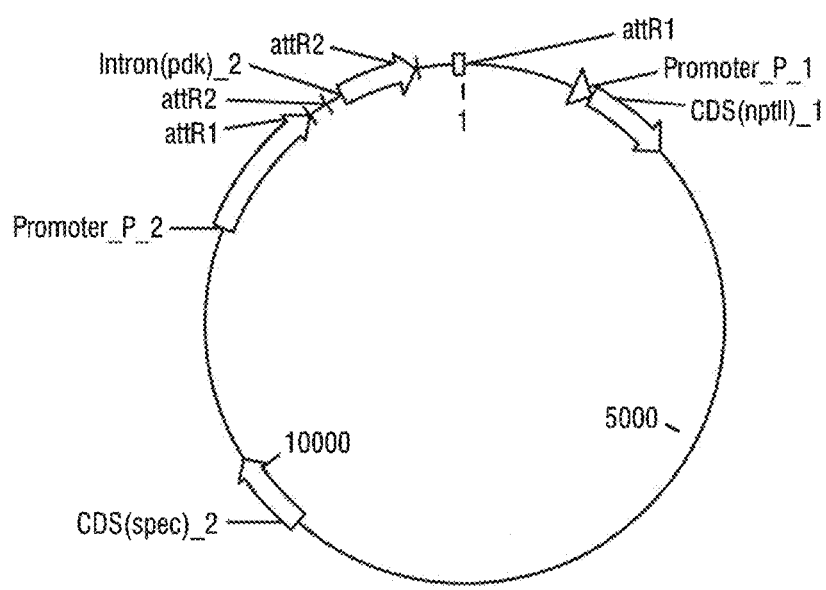

FIG. 3b shows the level of metabolites and gene expression for the auxin biosynthesis, metabolism and response pathway measured in wild type and lhy-10 Poplar trees. Metabolite (blue text) levels (pmoles/g F.W.) are shown over time (ZT hours) for wild type (black diamonds) and lhy-10 (open diamonds) plants. Error bars represent Standard deviation. Transcript (Black text) levels shown as boxplots for each probe set representing Poplar orthologs of the genes across all time points. lhy-10 (red) and WT (blue) levels shown next to each other for each probe set on the *Populus trichocarpa* microarray;

FIGS. 4A and 4B show the wood content of wild-type and lhy-10 poplar plants grown for 125 days under 18-hour light and 6-hour dark cycles; and FIG. 5A shows a map of an embodiment of a Gateway entry vector, pDONR201; and FIG. 5B shows a map of an embodiment of a destination vector, pHELLSGATE8.

DETAILED DESCRIPTION & EXAMPLES

The inventors studied the link between the activity of the circadian rhythm and the density of lignin within various plant species. Using microarray, they quantified gene expression, over time, in *Arabidopsis*, tobacco and poplar plants, as described in the Example 1. Based on gene ontology (i.e. a unified representation of gene and gene products across species), the inventors discovered that the known core clock gene LATE ELONGATED HYPOCOTYL, in *Arabidopsis*, and its orthologs, exhibited rhythmic expression in all three plant species. Given that LHY1 and LHY2 had already been identified as core clock genes which enable poplar plants to adapt their local environment (Takata et al., 2009. New Phytologist, 181: 808-819; Ibanez et al., 2010. Plant Physiology, 153: 1823-1833), the inventors decided to focus their research on the effect of LHY1 and LHY2 gene expression on lignin density within poplar plants. Using RNAi, the inventors created a transgenic poplar plant-line, referred to as lhy-10, which exhibits significantly reduced expression of both LHY1 and LHY2 genes compared to wild-type poplar plants, as described in Examples 2-8 (and FIGS. 1H, and 2-4). Among other characteristics, they measured the density of lignin within both plant species. The results of their research are described in the following Examples.

Example 1—Analysis of Rhythmic Gene Expression in *Arabidopsis*, Tobacco and Poplar Plants To determine whether rhythmic regulation of individual core circadian clock and circadian rhythm regulated genes was conserved across species, a comparison, over time, was made with orthologous genes expressed in *Arabidopsis*, tobacco and poplar plants. Gene expression in these plants was determined by microarray analysis and the results are shown in FIGS. 1A-D.

Growth Conditions

Rooted cuttings of in vitro cultivated Poplar wild-type and lhy-10 RNAi lines, as described in Example 2, were potted in a 3:1 mix of fertilized peat and perlite. Poplar plants were grown under 18-hour light/6-hour darks of 200 mol m$^{-2}$ s$^{-1}$ at 18° C. and 80% relative humidity. Tobacco plants were grown under cycles of 18-hour light and 6-hour dark for 54-56 days. *Arabidopsis* plants were grown under cycles of 12-hour light and 12-hour dark cycles for 9-10 days.

Isolation of Plant Tissue and RNA Extraction

Tissue samples were collected from internodes 8-11 of leaf blades from independent wild-type *Populus tremula*×*P. tremuloides* T89 cultivar and transgenic poplar lhy-10 trees where the level of PttLHY1 and PttLHY2 genes were down-regulated by RNAi interference, as described in Example 2. The resulting RNA was purified and DNAse treated as described in Kozarewa et al., 2010 (Plant Molecular Biology, 73: 143-156). Expression of the core clock genes PttLHY1 and PttLHY2 was investigated by real-time PCR as reported in Ibanez et al., 2010 (Plant Physiology, 53: 1823-1833).

Gene expression, over time, was determined by microarray. RNA was harvested 3 hours before dawn and up to 48 hours later. Pools of RNA were used to hybridize with the Affymetrix *Populus* array. Hybridisations were carried out by Nottingham *Arabidopsis* Stock Centre (NASC) array facility. Reference wild-type genomic DNA for the microarray analysis was obtained from leaf tissue by hexadecyl trimethyl ammonium (CTAS) extraction as described by Chang et al., 1998 (Plant Mol. Biol. Rep., 11: 113-116).

Microarray Analysis

Microarray analysis was carried out as described in Edwards et al., 2006 (Plant Cell, 18(3): 639-50).

Microarray Annotations

Information on *Populus* genes, including mapping to *Arabidopsis* orthologs, were based on annotations from the PopARRAY database. Comparisons with *Arabidopsis* were based on microarray data on the *Arabidopsis* Affymetrix ATH1 whole genome array. Only probe sets which could be unambiguously mapped to individual *Arabidopsis* genes, based on the TAIR 7 annotations, were included in the analyses (www.arabidopsis.org).

Results

Figure 1B:
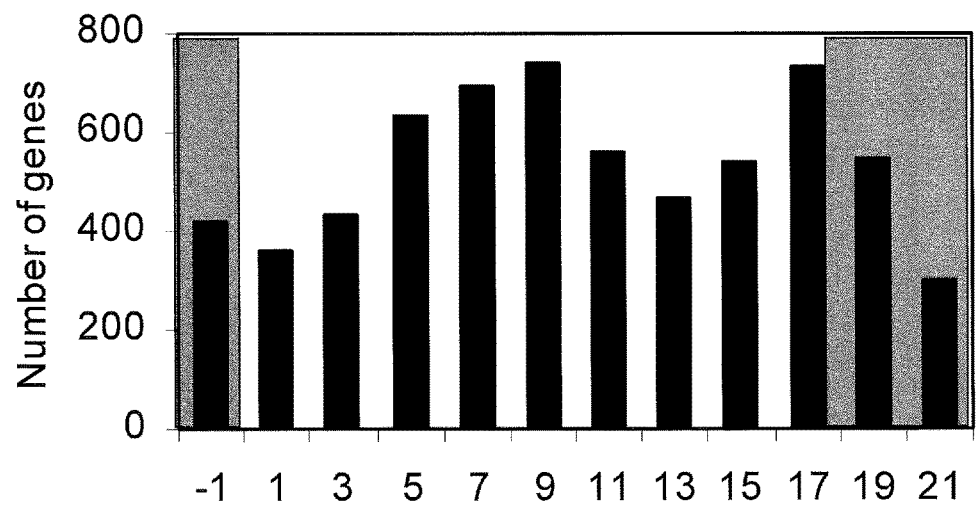
FIG. 1B shows a histogram of peak phase gene expression of 54-56 day old tobacco plants grown under cycles of 18-hour light and 6-hour dark.
Figure 1C:
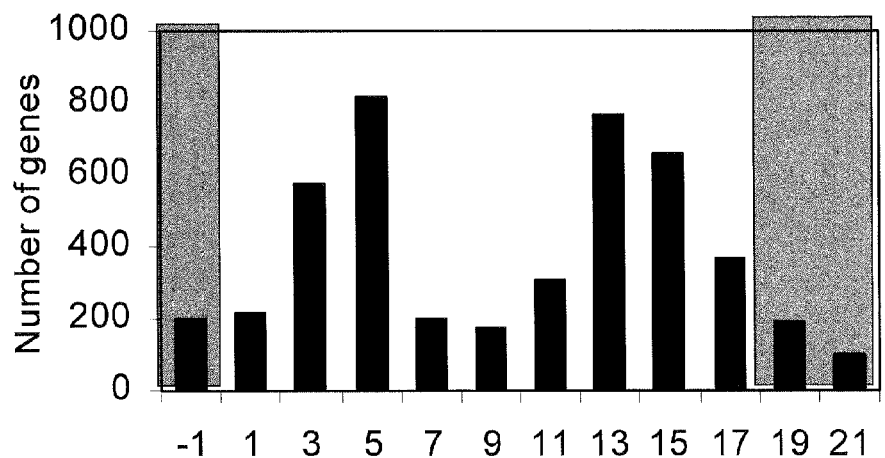
FIG. 1C shows the gene expression, over a single diurnal cycle, of wild-type poplar plants grown under 18-hour light and 6-hour dark cycles at 18° C. and 80% humidity for 40-42 days.
Figure 1D:
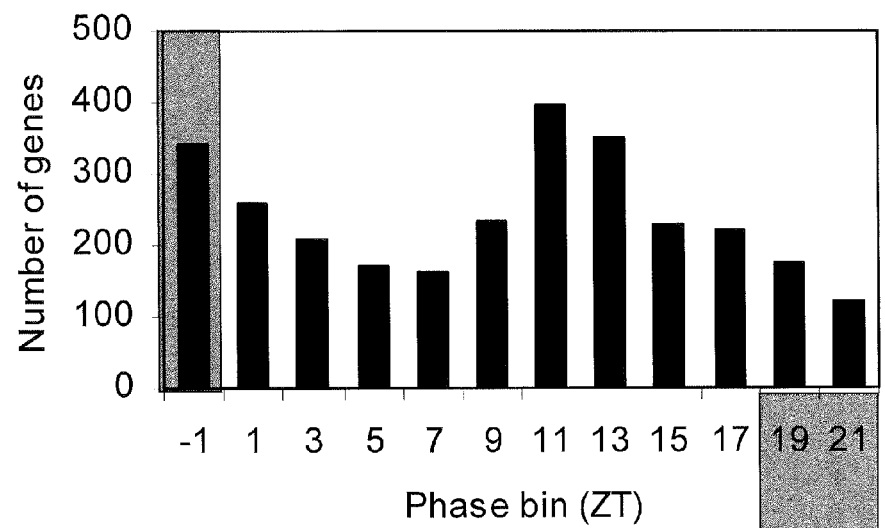
FIG. 1D shows the gene expression, over a single diurnal cycle, of lhy-10 poplar plants grown under 18-hour light and 6-hour dark cycles at 18° C. and 80% humidity for 40-42 days.

FIGS. 1A-C summarise the level of gene expression that occurred, over time, in *Arabidopsis*, tobacco and poplar plants. Both tobacco and poplar plants exhibited rhythmic expression of genes with two main peak phase times. For tobacco plants, the peak phase times were the middle of the day (Zeitgeber Time [ZT] 7-9 hours) and around dusk (ZT 17 hours), as shown in FIG. 1B. For poplar plants, the peak phase times were just after dawn (ZT 3-5 hours) and towards dusk (ZT 13-17 hours), as shown in FIG. 1C. Targeting of rhythmic gene expression towards subjective dusk was also shown in *Arabidopsis* in a previous study under free-running circadian conditions (FIG. 1A; Edwards et al., 2006. Plant Cell, 18(3):639-50).

Figure 1F:
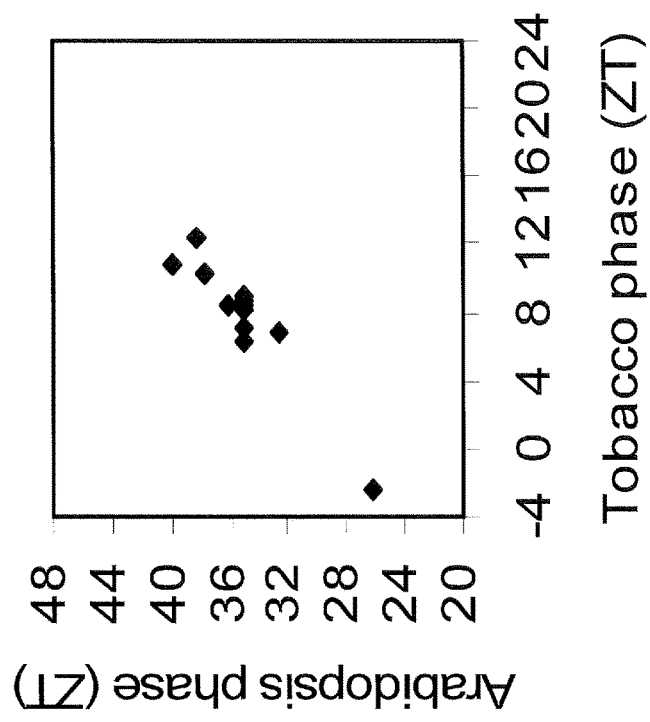
FIG. 1F shows the correlation between the phase expression of core clock genes in *Arabidopsis* and tobacco plants.

To determine whether the rhythmic regulation of individual genes was conserved across species, 12 core circadian clock genes of poplar and tobacco plants, as listed in Table 1, were compared to known orthologs present in *Arabidopsis*. It was found that that there is a strong conservation of rhythmic gene expression for *Arabidopsis* clock orthologs in other plant species. The phase (i.e. time point at which the genes are expressed) of these core clock genes was also strongly conserved across the species, as shown in FIGS. 1F and 1G. This conservation was slightly stronger in tobacco plants and may partially be explained by the more pronounced expression of genes towards the dawn and dusk phases in wild-type poplar plants, as shown in FIGS. 1C, F and G.

The strong conservation of phase in core circadian clock genes suggested that the core circadian clock gene network was relatively conserved between species. However, there was no evidence of global conservation of phase for orthologous clock-controlled genes across species. This suggests that the out-put pathways of these core circadian clock genes are less conserved and more sensitive to environmental factors, such as the timing of dawn and dusk, which is consistent with previous results shown in *Arabidopsis* (Edwards et al., 2010. Molecular Systems Biology, 6:424).

Individual circadian rhythm regulated genes did not show phase conservation across species, however, there was evidence that the timing of certain biological activities was conserved. Table 1 summarizes the results of Gene Ontology analysis of core circadian clock genes clustered by phase.

TABLE 1

Gene Ontology analysis and phase expression of core circadian clock genes expressed in *Arabidopsis*, Tobacco and Poplar plants

| Core Clock Gene | *Arabidopsis* Peak Phase (hours)* | Tobacco Peak Phase (hours) | Poplar Peak Phase (hours) | Poplar lhy-10 Peak Phase (hours) |
|---|---|---|---|---|
| LHY | 2.238 (26.238) $ | −2.322 | 3.856 (LHY1) | 0.69 |
|  |  |  | 4.8 (LHY2) | 0.46 |
|  |  |  | 4.56 (LHY1) | NR * |
| CCA1 | 2.711 (26.711) $ | NO * | NO * | NO * |
| TOC1 | 14.296 (38.296) $ | 12.3 | 11.856 | 9.66 |
| GI | 11.048 (35.048) $ | 6.425 | 12.152 | NR * |
|  |  | 8.917 |  |  |
|  |  | 8.024 |  |  |
|  |  | 8.382 |  |  |
|  |  | 8.568 |  |  |
|  |  | 7.084 |  |  |
| PRR3 | 13.66 (37.66) $ | NO * | NO * | NO * |
| PRR5 | 12.062 (36.062) | 8.54 | 11.289 | NR * |
|  |  |  | 10.998 | 6.728 |
|  |  |  | 11.388 | 7.752 |
| PRR7 | 8.699 (32.699) $ | 6.864 | 12.449 | 10.56 |
|  |  |  | 12.027 | 10.512 |
|  |  |  | 13.38 | 10.53 |
| PRR9 | 6.332 (30.332) $ | NO * | 6 | NR * |
|  |  |  | 8.136 | NR * |
|  |  |  | 8.019 | NR * |
| ELF3 | 15.98 (39.98) $ | NR * | NR * | NR * |
| ELF4 | 15.978 (39.978) $ | NO * | 13.5 | 11.395 |
| TIC | NP * | NR * | NO * | NO * |
| LUX | 13.66 (37.66) $ | 10.332 | NR * | NR * |

* NO - No known ortholog in the species; NP - No probeset for gene present on array; and NR - Not Rhythmic - Gene not scored rhythmic in experiment.
$ *Arabidopsis* phase estimates are provided from Edwards et al., (2006 Plant Cell). Values presented have been adjusted to be comparative to Poplar and Tobacco phase estimates by the subtraction of 24 h as this was a circadian experiment (original phase estimates shown in parentheses).

Example 2—Generation of Transgenic Poplar Lhy-10 Plants

The gene LATE ELONGATED HYPOCOTYL1 is known. It is expressed in *Arabidopsis* and codes for a transcription factor that regulates the transcription of circadian rhythm regulated genes. Molecular studies on *Populus tremula×P. tremuloides* have identified LHY1 and LHY2 as core circadian clock genes which enable poplar plants to adapt their local environment by regulating the expression of other rhythmically expressed genes and altering their perception of photoperiod (day length). LHY1 and LHY2 are crucial for aligning major growth events with long days and warm temperatures in spring and summer, and the ability to obtain freezing tolerance during dormant periods.

In order to study the effect of the circadian rhythm on the growth and development of poplar plants, a transgenic poplar plant cell line, referred to as lhy-10, which exhibits significantly reduced expression of both LHY1 and LHY2 genes compared to its wild-type poplar plants grown in the same conditions, was created. lhy-10 was created by the transformation of *Populus tremula×P. tremuloides* clone T89 with RNAi constructs, as described in Eriksson et al., 2000 (Nat Biotechnology, 18: 784-788).

SEQ ID NO.1 and SEQ ID NO.3 were obtained from *Populus* cDNA (*Populus tremula×P. tremuloides*) by amplification with Platinum Pfx DNA polymerase (Invitrogen) and the primers, as represented by SEQ ID NO.6 and SEQ ID NO.7. Both primers include Gateway specific sequences, which are underlined.

```
                                           SEQ ID NO. 6
GGGGACAAGTTTGTACAAAAAAGCAGGCATGGAAATATTCTCTTCTGGG
(Forward primer for LHY1 and 2)

SEQ ID NO. 7
GGGGACCACTTTGTACAAGAAAGCTGGGTTTGTCCTATTGGAACACCTT
(Reverse primer for LHY1 and 2)
```

DNA fragments were cloned into Gateway entry vector pDONOR201, as shown in FIG. 5a, and then recombined into the plant binary destination vector pHELLSGATE8, as shown in FIG. 5b (see Helliwell et al., 2002. Funct. Plant Biol., 29: 1217-1225), using Gateway BP Clonase enzyme mix (Invitrogen). The respective plasmids were transformed into the *Agrobacterium tumefaciens* C58 strain GV3101 (pMP90RK), which is a disarmed Ti plasmid in which the T-regions have been deleted.

RNAi

A single RNAi sequence that targets both PttLHY1 and PttLHY2 was created. The RNAi sequence is represented by SEQ ID NO.5 and was created using SEQ ID NO.1 and SEQ ID NO.3 as templates, as described in Ibanez et al., 2010 (Plant Physiology, 153: 1823-1833).

SEQ ID NO.5 was used to down-regulate the expression of both PttLHY1, as represented by SEQ ID NO.1, and PttLHY2, as represented by SEQ ID NO.3.

Generation of Transgenic lhy-10 Poplar Plants

*Populus tremula×P. tremuloides* clone T89 transformed with the RNAi constructs targeted towards PttLHY1/PttLHY2 were regenerated as described in Eriksson et al., 2000 (Nat Biotechnology, 18: 784-788). Ten independent kanamycin-resistant lines were isolated and characterized per construct.

Example 3—Analysis of Rhythmic Gene Expression in Wild-Type and Lhy-10 Poplar Plants As shown in Table 2, some biological activities, such as Abscisic acid responses and preparation for photosynthesis, are conserved across the different species of plant, to specific times of the day.

TABLE 2

Biological activities regulated by the circadian rhythm of *Arabidopsis*, Tobacco and Poplar plants.

| Zeitgeber time (hours) | *Arabidopsis* | Tobacco | Poplar |
|---|---|---|---|
| 0-4 | Abscisic acid responses | Abscisic acid responses<br>Preparation for photosynthesis<br>Phenylpropanoid biosynthesis | Preparation for photosynthesis<br>Regulation of cell division<br>Nitrogen assimilation/metabolism |
| 4-8 | Long day photoperiodism<br>Carbohydrate metabolism<br>Photosynthesis related<br>Water channel activity | Long day photoperiodism<br>Photosynthesis<br>Growth?<br>Brassinosteroid biosynthetic process<br>Photosynthesis<br>Response to sugars<br>Cell wall modification<br>Stress responses (drought, high light intensity | Red and far red light responses<br>Pentose Phosphate shunt<br>Lipid binding and transport |
| 8-12 | Response to cold and salt stress<br>Response to sugars | Response to cold, salt and other organisms?<br>Photosynthetic activity<br>Carbohydrate metabolism<br>DNA unwinding<br>Nucleosome assembly | Anthocyanin biosynthesis<br>Glycolipid binding and transport<br>Polysaccharide metabolism<br>Response to hormone stimulus (JA, GA, ABA, ethylen)<br>Secondary cell wall synthesis |
| 12-16 | Photosynthesis dark reactions | Chlorophyll catabolism<br>Chlorophyll biosynthesis<br>Response to high light intensity<br>Chlorophyll biosynthesis<br>Fatty acid biosynthesis | Glucose metabolism<br>Pentose phosphate shunt<br>Starch biosynthesis<br>Amino acid transport<br>Chlorophyll catabolism<br>Carbohydrate transport |
| 16-20 | Carbohydrate metabolism | Response to blue, red and far-red light<br>Carotenoid biosynthesis<br>Photosynthetic electron transport<br>Nitrate assimilation<br>Starch breakdown<br>Translational machinery<br>Pentose phosphate shunt | Cytokinin receptor activity<br>Shoot and root development/growth<br>Chlorophyll catabolism<br>Response to wounding and biotic stresses |
| 20-24 | Chlorophyll, phenylpropanoid and xanthophyll biosynthesis<br>Lignin biosynthesis<br>Amino acid metabolism<br>Sulfate assimilation | Chlorophyll and xanthophyll biosynthesis<br>Starch breakdown<br>Cellulose biosynthesis<br>Auxin response<br>Cation transport<br>Regulation of cell division<br>Sugar transport<br>Phospholipid biosynthesis | Proanthocyanidin biosynthesis<br>Starch breakdown and carbohydrate transport<br>Auxin binding/response<br>Blue light responses<br>Cell wall organisation<br>Nitrate transport<br>Sugar transport |

This suggests that there is a selective advantage to this temporal co-ordination. To determine whether temporal co-ordination occurs in poplar plants, the transgenic Poplar line, lhy-10, as described in Example 2, was grown and sampled for microarray analysis in comparison to wild-type poplar tress (Ibáñez et al., 2010, Plant Physiology, 53: 1823-1833).

Growth Conditions

The growth conditions used were identical to those used in Example 1.

Figure 1E:
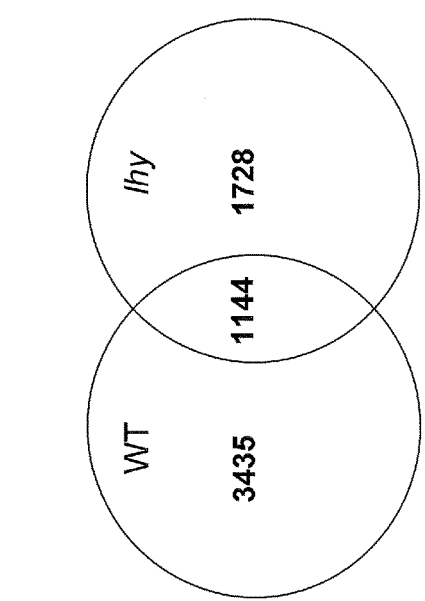
FIG. 1E shows a Venn diagram of the number of rhythmically expressed genes as scored by the program COSOPT with a pMMC-Beta threshold of <0.05 (See Edwards et al., 2006, Plant Cell, 18(3):639-50) in wild-type and/or lhy-10 poplar plants.
Figure 1H:
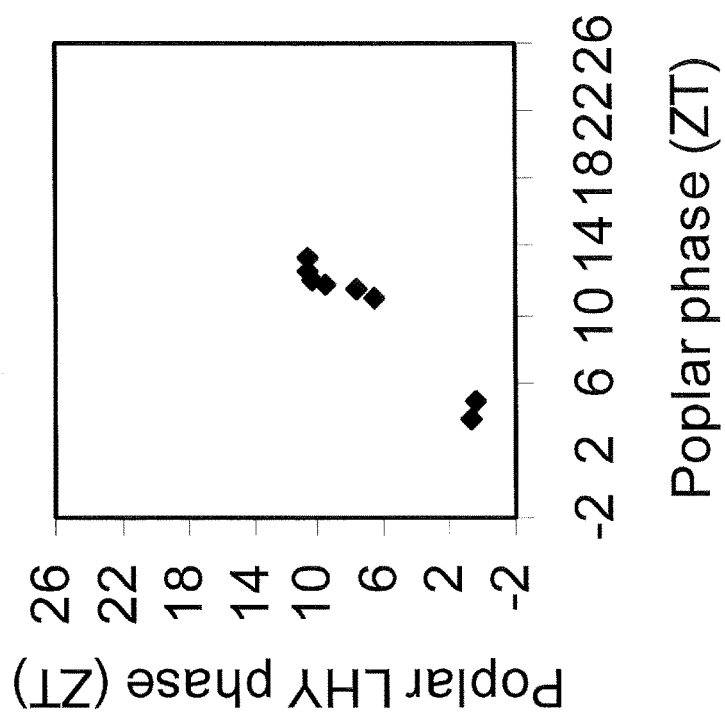
FIG. 1H shows the correlation between the phase expression of core clock genes in wild-type and lhy-10 poplar plants.
Figure 1G:
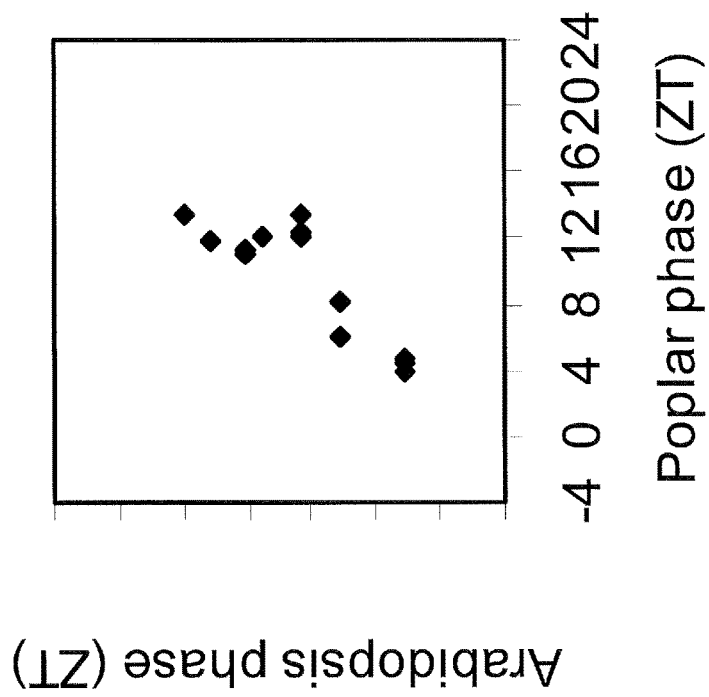
FIG. 1G shows the correlation between the phase expression of core clock genes in *Arabidopsis* and wild-type poplar plants.

Results 4579 genes were identified as rhythmic in wild-type poplar plants, while only 2872 genes were identified as rhythmic in the lhy-10 line, as shown in FIG. 1E. Interestingly, a sub-set of 1728 genes which were rhythmically expressed in the lhy-10 mutant were not rhythmically expressed in wild-type poplar plants.

Despite being the target of siRNA, low levels of endogenous LHY1 and LHY2 genes were rhythmically expressed in the lhy-10 RNAi line, as shown in Table 1 (and Ibáñez et al., 2010, Plant Physiology, 53: 1823-1833). However, the phase of their expression was earlier than the phase of expression in wild-type plant plants. As expected, due to the use of siRNA, these two genes also showed lower expression and amplitude in lhy-10 poplar plants. The peaks in their expression were much narrower and not maintained as late into the day when compared to wild-type poplar plants. Other clock genes PSEUDO RESPONSE REGULATOR 9 (PRR9), GIGANTEA (GI), EARLY FLOWERING 3 (ELF3) and LUX ARRHYTMIO (LUX) also exhibited arrhthymic expression in the lhy-10 plants. This suggests that the circadian clock network was perturbed, particularly the morning loop (ZT 3-5 hours) and its directly regulated genes (see table 1). This observation was further supported by the loss of the post-dawn peak phase by lhy-10 that was exhibited in wild-type poplar plants at ZT 3-5 hours, as shown in FIGS. 1C and D. Only the evening phase of expression was maintained in the mutant, albeit slightly earlier as might be expected for a short period mutant.

Example 4—Analysis of Wild-Type and Lhy-10 Poplar Plant Height and Stem Diameter As shown in Table 2, biological activities associated with cell division and growth seem to be targeted towards the end of the night and early part of the day in tobacco, *Arabidopsis* and Poplar. Perturbation of this temporal regulation may therefore have an affect on the growth rate of these plants.

Figure 2A:
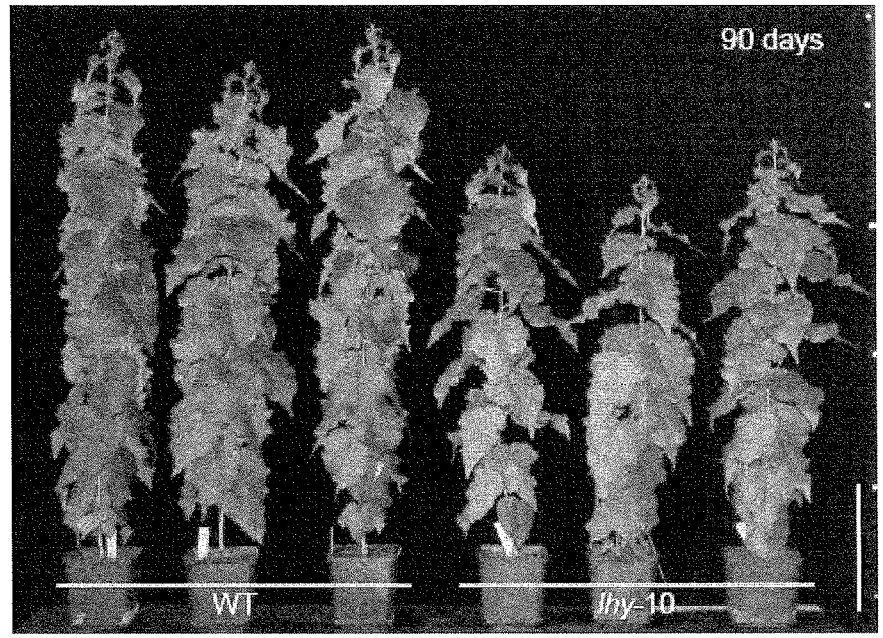
FIG. 2A shows the height of wild-type and lhy-10 poplar plants after growth under 90 days worth of 18-hour light and 6-hour dark cycles at 18° C. and 80% humidity.
Figure 2B:
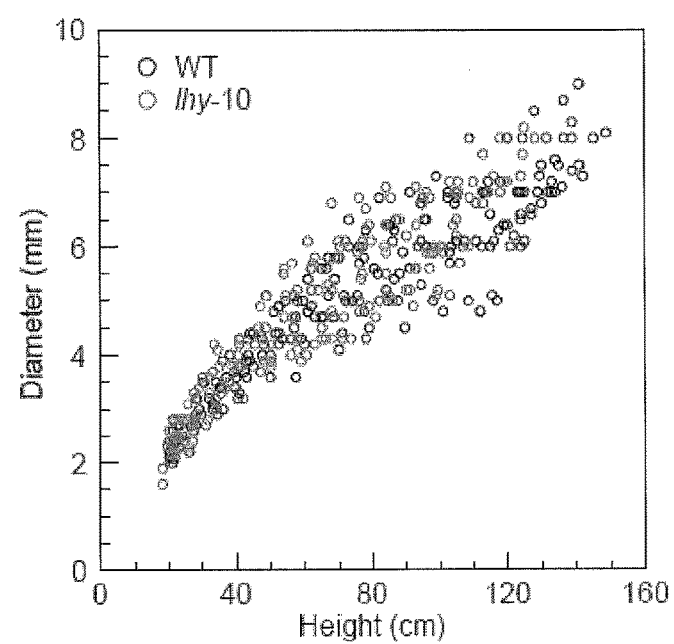
FIG. 2B shows the correlation between height and diameter of wild-type and lhy-10 poplar plants grown for 90 days under 18-hour light and 6-hour dark cycles.
Figure 2C:
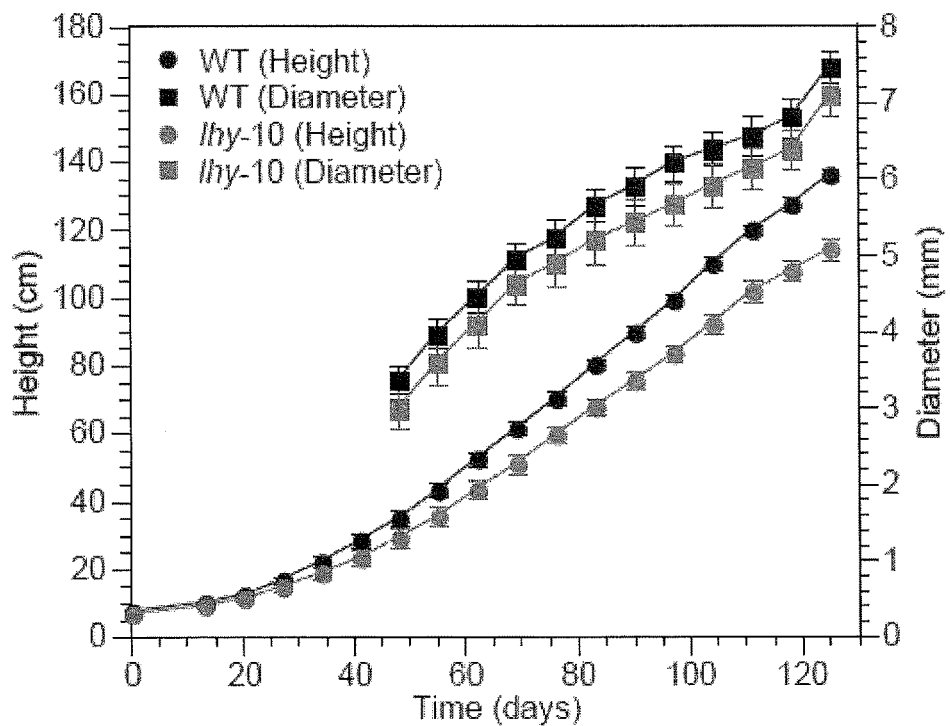
FIG. 2C shows the height and diameter of wild-type poplar and lhy-10 poplar plants grown for 40-42 days under 18-hour light and 6-hour dark cycles at 18° C. and 80% humidity.

To determine the effect of perturbation of the circadian rhythm on the height and diameter of in Poplar plants, the height and diameter of wild-type and lhy-10 poplar plants were measured over time, as shown in FIGS. 2A-2C.

Growth Conditions

Rooted cuttings of in vitro cultivated wild-type and lhy-10 RNAi lines were potted in a 3:1 mix of fertilized peat and perlite. Plants were grown under 18-hour light/6-hour darks of 200 μmol m$^{-2}$ s$^{-1}$ at 18° C. and 80% relative humidity for 90 days (FIGS. 2A and 2B) or 125 days (FIG. 2C).

Growth Analyses

The height of each plant was measured every week after three weeks of the potting. At the end of the experiment, their diameters were also measured 10 cm above the soil using a digital caliper. The elongation growth rate of plants were evaluated by a curve-fitting procedure. Curves were fitted to the growth patterns of each plant using the linearized biexponential model ($y=\eta \ln [e^{\alpha_1(t-\tau_c)/\eta}+e^{\alpha_2(t-\tau_c)/\eta}]+\chi$; y, height; η, smoothness/abruptness of the curve; $\alpha_1$, slope of the first linear; t, time; $\tau_c$, constant for shifting along the t; $\alpha_2$, slope of the second linear that represents the growth rate; χ, constant for shifting along the y) (Buchwald, 2007) using Kaleidagraph ver. 30.6.

In additional experiments, the density of internodes in both wild-type and lhy-10 poplar plants was determined, as shown in Table 3. Twelve wild-type and twelve lhy-10 plants were grown as described above. Height measurements were taken at weekly intervals, while the diameter was measured at the end point of the experiment. At the end of the experiment, the plants were than harvested, stem samples were collected from internodes 15 and 16 as described by Eriksson et al., 2000 (Nat Biotechnology, 18: 784-788). Under green safe light, the samples were weighed, measured and fixed in FAA (50% Ethanol, 10% Formaldehyde and 5% Acetic acid) for anatomical inspection at ZT1 (one hour after the lights had been turned on) and ZT19 (one hour after the lights had been turned off). Also, all remaining leaves, stems and root parts were collected separately from each individual plant (i.e. not pooled) and weighed immediately. Following three days of drying at 55° C., the remaining leaves, stems and root parts were weighed once again to determine the dry and weight of each tissue, in addition to their biomass, as shown in Table 3.

Results

After 90 days of growth in photoperiodic conditions, there was a significant difference in the appearance of wild-type and lhy-10 poplar trees, as shown in FIG. 2A. Wild-type plants were significantly taller and had larger stems than the lhy-10 poplar plants. Therefore they had a greater volumetric index of growth, as shown in Table 3. However, the height/diameter ratio of both genotypes was similar, as shown by FIG. 2B. Consistent with this, the number of internodes initiated under a 13 day period were counted in the morning at Zeitgeber time 1 (ZT1; 1 hour after the lights were turned on) and found to be similar in wild-type and lhy-10 plants, with value of 23.17±0.31 and 22.67±0.38 respectively. However, when a different cohort of plants were counted at night, ZT19 (1 hour after the lights were turned off), the wild-type plants had a slightly increased number of internodes, 23.83±0.31, compared with the lhy-10 polar plants, 22.67±0.42.

Figure 2D:
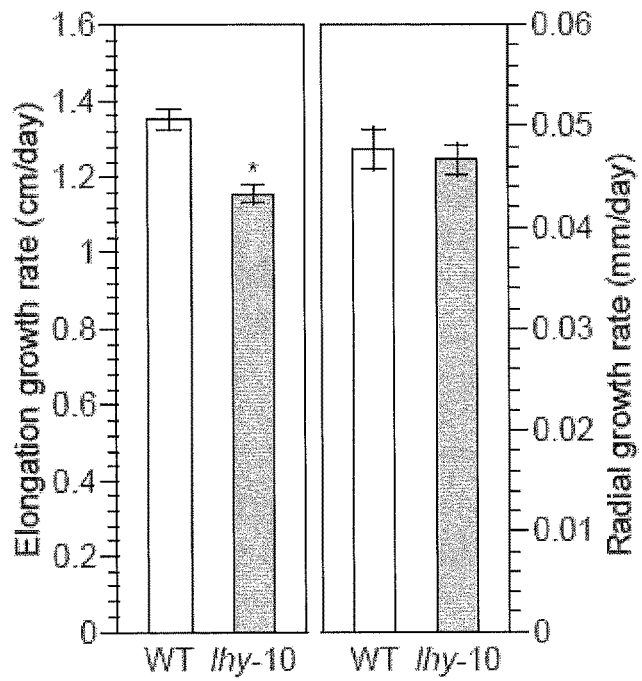
FIG. 2D shows the elongation growth rate and radial growth rate of wild-type poplar and lhy-10 poplar plants grown under 40-42 day worth of 18-hour light and 6-hour dark cycles at 18° C. and 80% humidity.

Thus, the developmental programme was similar in both poplar plant genotypes, but cellular activity relating to cellular elongation and diameter growth are specifically affected. Their rate of growth, in height, was similar during the first four weeks of exposure to the photoperiodic conditions, but deviated thereafter, as shown in FIG. 2C. The rate of growth, in the diameter was not affected, as shown in FIG. 2D.

As shown in Table 3, wild-type poplar plants have a significantly greater volume and biomass than lhy-10 poplar plants.

TABLE 3

A summary of the effect of LHY1 and LHY2-gene down-regulation on the growth and biomass of poplar plants.

| | Wild-type poplar | lhy-10 poplar plants |
|---|---|---|
| Index of volumetric growth (mm$^3$) | 5783.7 ± 684.8 | 3422.6 ± 306.5* |
| Density of internodes 15 and 16 (g/cm3) | | |
| ZT1 | 1.268 ± 0.075 | 1.387 ± 0.056 |
| ZT19 | 1.536 ± 0.013 | 1.467 ± 0.102 |
| Dry weight biomass (g) | | |
| Leaf | 8.934 ± 1.036 | 5.031 ± 0.364* |
| Stem | 7.265 ± 0.899 | 3.996 ± 0.379* |
| Root | 5.539 ± 0.748 | 3.186 ± 0.437* |

TABLE 3-continued

A summary of the effect of LHY1 and LHY2-gene down-regulation on the growth and biomass of poplar plants.

|  | Wild-type poplar | lhy-10 poplar plants |
|---|---|---|
| Fresh weight biomass (g) | | |
| Leaf | 40.313 ± 4.545 | 24.139 ± 1.701* |
| Stem | 30.105 ± 3.656 | 17.689 ± 1.579* |
| Root | 41.646 ± 5.418 | 22.673 ± 2.770* |

*$P < 0.01$

Example 5—an Anatomical Assay of Wild-Type and Lhy-10 Poplar Plant Fibre and Vessel Cell Dimensions Cambium cells are partially differentiated vascular cells. An increase in the number of these cells present within a plant tissue is an indication of cellular division. Therefore, in order to compare the amount of cellular division occurring within wild-type and lhy-10 poplar plants, tissue node samples were taken from both groups of plants and the number of cambium cells were counted, as shown in FIGS. 2E, 2F and 2G.

Tissue samples were taken from internode 16 of plants of plants at ZT1 and ZT19, after being grown for 125 days under 18-hour light/6-hour dark cycles of 200 µmol m$^{-2}$ s$^{-1}$ at 18° C. and 80% relative humidity. The diameter of mid internode 16 was measured using a digital caliper. The samples were fixed in a FAA solution (50% Ethanol, 10% Formaldehyde and 5% Acetic acid), sequentially dehydrated through a 50, 75 and 100% ethanol series, and then embedded in LR White (TAAB) in polypropylene capsules (TAAB). Three micrometer thin section were obtained using a Microm HM350 microtome (Microm International) and heat-fixed to glass slides. The sections were stained with toluidine blue and mounted in Entellan neu (Merck). Images were visualized using a Zeiss Axioplan light microscope (Zeiss) attached with an Axiocam digital camera (Zeiss). The number of cambium cells was counted from 50 cambial cell files from six trees per each line at same time point.

Results

Figure 2E:
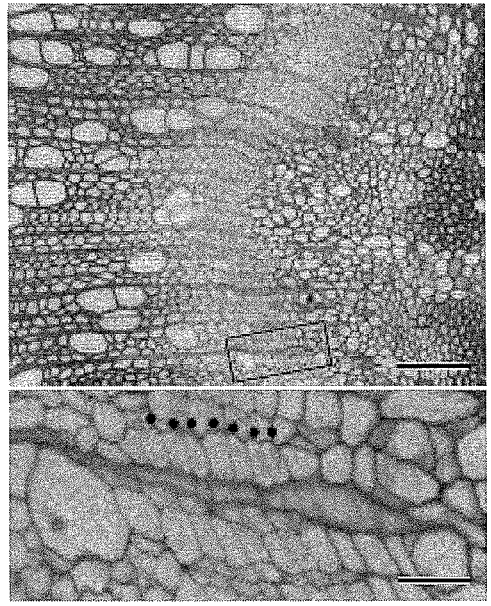
FIG. 2E shows cambium and fibre cells of wild-type and lhy-10 poplar plants grown for 40-42 days under 18-hour light and 6-hour dark cycles at 18° C. and 80% humidity.
Figure 2E:
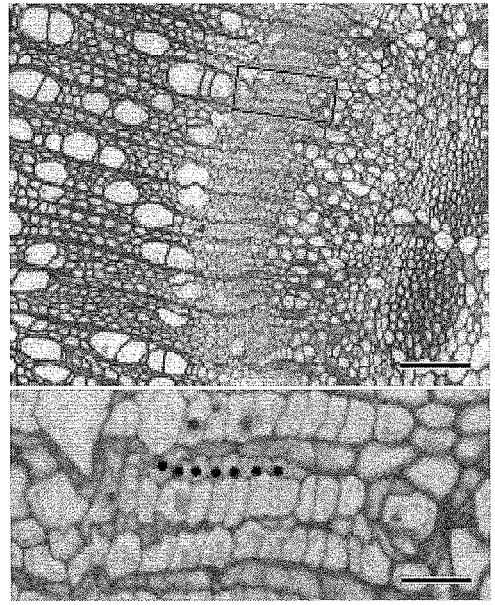
Figure 2E:
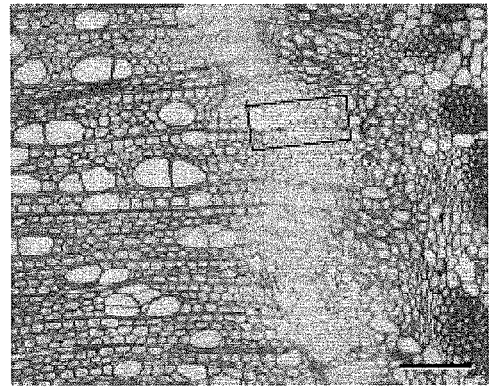
Figure 2E:
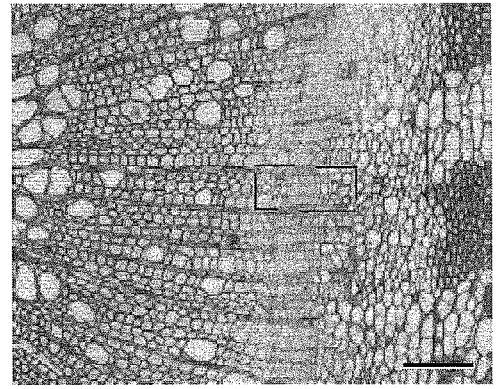
Figure 2F:
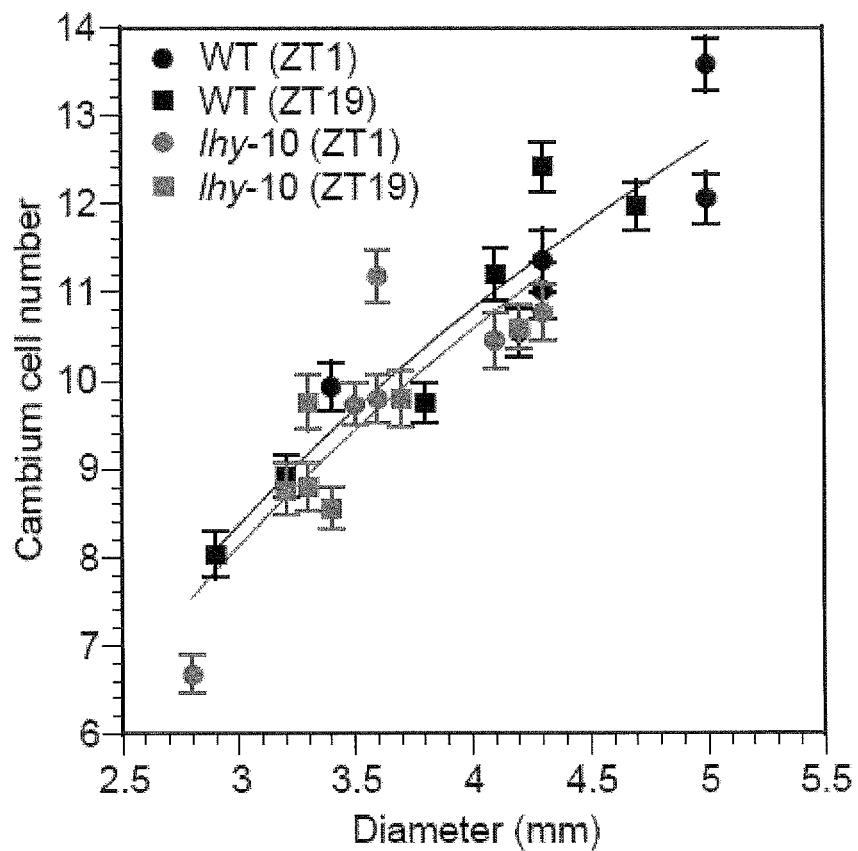
FIG. 2F shows the correlation between the change in cambium cell number and diameter in wild-type and lhy-10 poplar plants grown for 40-42 days under 18-hour light and 6-hour dark cycles at 18° C. and 80% humidity.
Figure 2G:
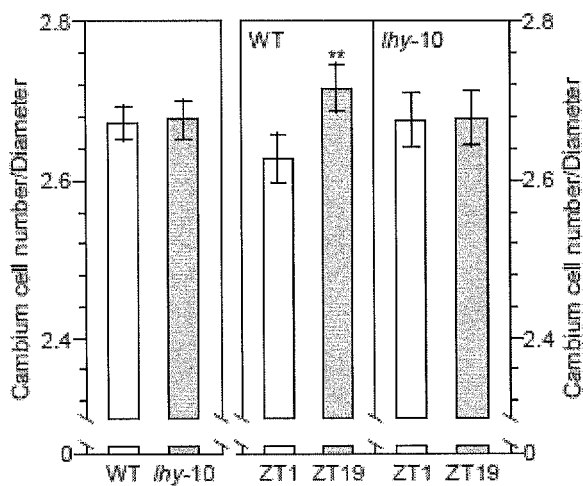
FIG. 2G shows the correlation between the change in cambium cell number and diameter in wild-type and lhy-10 poplar plants grown for 40-42 days under 18-hour light and 6-hour dark cycles at 18° C. and 80% humidity.

The number of cambium cells and the ratio of cambium cells to cellular diameter was similar in both wild-type and poplar lhy-10 plants, as shown in FIGS. 2E and 2G. However, unlike wild-type poplar plants, lhy-10 plants did not exhibit any diurnal variation in cambium cell division, as shown in FIG. 2E).

Example 6—Expression of Cytokinin and Auxin-Related Genes in Wild-Type and Lhy-10 Poplar Plants Cytokinins and auxins are plants hormones, which are believed to important for plant cell elongation, cell division and wood formation in poplar trees. They are produced in actively growing tissues and effect the growth of apical, cambium and root meristems. Gene Ontology analysis, as shown in Table 1, revealed that a large number of genes which play a role in auxin and cytokinin responses, are actively expressed between dusk and dawn in wild-type poplar plants. Therefore, in order to determine whether LHY1 and LHY2 genes regulate the expression of cytokinin and auxins in poplar plants, the expression of genes-related to cytokinin was determined in wild-type and lhy-10 poplar plants, as shown in FIGS. 3A and 3B.

Tissues for measurements were extracted from actively growing leaves off internodes 8-10 with the first internode being a leaf primordial of at least 1 cm.

Growth Conditions

Rooted cuttings of in vitro cultivated wild-type and lhy-10 RNAi lines were potted in a 3:1 mix of fertilized peat and perlite. Plants were grown under 18-hour light/6-hour darks of 200 µmol m$^{-2}$ s$^{-1}$ at 18° C. and 80% relative humidity for 40-42 days before harvest.

Auxin Extraction and Measurements

For auxin measurements three independent biological pools of four leaves as biological replication and with three technical replications of these samples collected independently parallel to and partially overlapping with the samples for microarray analysis.

Cytokinin Extraction and Measurements

Likewise for cytokinin measurements, material sampled in parallel and constituting part of pool used for the microarray with one biological pool replication per time point and three technical replications over 48 hours.

Results

The pattern and level of expression of genes involved in cytokinin metabolism did not shown any significant differences between WT and lhy-10 plants, as shown in FIG. 3a. However, a difference was observed in the level of several classes of cytokinins, in particular the trans- and cis-Zeatins along with the Topoline-classes. In contrast, no difference was shown in the abundance of auxin metabolites, IAA or oxIAA, or expression levels for genes involved in the Auxin biosynthesis pathway, as shown in FIG. 3b.

Example 7—Measurement of the Lignin Content of Wild-Type and Lhy-10 Poplar Plants The development of wood in plants is dependent on the concentration gradient of auxin within the plant. Given that metabolism of auxin in the lhy-10 mutant plants was not significantly different to wild-type poplar plants, as shown in Example 7 and FIG. 3b, the lignification zone of wild type and lhy-10 trees at internode 16 was analysed.

To visualize lignified fibres in 10 micrometer sections from internode 16 were stained with phloroglucinol, as shown in FIG. 4.

Results

Mutant lhy-10 poplar trees had a higher density of lignified wood than their wild-type counterparts, as shown in FIG. 4. This is due to the following two reasons. Firstly, the size of the lignification zone in lhy-10 poplar plants being similar to that of wild-type poplar plants. This is in line with finding that auxin levels, were not significantly affected by the knock-down of LHY1 and LHY2 genes, as shown in Example 7. Auxin is important in cell division and secondary cell wall biosynthesis is dependent on a gradient of auxin over the cambium. For instance overexpression of auxin decreases cell division and increase the extent of xylem wood. Secondly, the overall biomass of the thy-10 poplar plants was significantly reduced in comparison to their wild-type counterparts, as shown in FIG. 2A, which may be due to the reduced level of cytokinin, as shown in FIG. 3a.

The invention claimed is:

1. A method of modulating the density of lignin in a test plant compared to the corresponding lignin density in a wild-type plant cultured under the same conditions, the method comprising:
introducing to said plant or an ancestor thereof a polynucleotide construct designed to modulate the concentration and/or activity of a LATE ELONGATED HYPOCOTYL 1 (LHY 1) and a LATE ELONGATED HYPOCOTYL 2 (LHY 2) gene wherein said LHY 1 gene comprises a nucleic acid sequence as set forth in SEQ ID NO:1 or a sequence with at least 90% sequence identity thereto, and said LHY 2 gene comprises a nucleic acid sequence as set forth in SEQ ID NO:3 or a sequence with at least 90% sequence identity thereto, and thereafter,
regenerating said plant, wherein said modulation is decreasing the concentration and/or activity of the polypeptide encoded thereby and lignin density is increased, or wherein said modulation is increasing the concentration and/or activity of the polypeptide encoded, thereby decreasing lignin density.

2. The method of claim 1, wherein the polypeptide encoded by the LATE ELONGATED HYPOCOTYL 1

(LHY 1) gene comprises the amino acid sequence of SEQ ID NO:2, or an amino acid sequence with sequence identity which is greater than 90% to SEQ ID NO: 2 and the polypeptide encoded by the LATE ELONGATED HYPOCOTYL 2 (LHY 2) gene comprises the amino acid sequence of SEQ ID NO: 4 or an amino acid sequence with sequence identity greater than 90% to SEQ ID NO: 4.

3. A method according to claim 1, wherein increasing lignin density is achieved by decreasing the concentration and/or activity of the polypeptide encoded by the LATE ELONGATED HYPOCOTYL 1 (LHY 1) gene and/or the LATE ELONGATED HYPOCOTYL 2 (LHY 2) gene by:
 (i) decreasing, preventing or attenuating transcription, translation or expression of the gene;
 (ii) inhibiting synthesis of the polypeptide encoded by the gene; or
 (iii) increasing the rate of degradation of the polypeptide encoded by the clock gene.

4. The method according to claim 1, wherein the method comprises decreasing the concentration of the polypeptide encoded by the LHY1 and/or LHY2 gene using RNAi.

5. The method according to claim 1, wherein the method comprises transforming a cell of the test plant with an RNAi molecule which is capable of down-regulating the expression of the —LHY1 and LHY2 gene.

6. The method according to claim 5, wherein the RNAi molecule comprises a small interfering RNA (siRNA) molecule, or a short hairpin loop (shRNA) molecule.

7. The method according to claim 5, wherein the RNAi molecule of the invention comprises a nucleotide sequence as set out in SEQ ID NO:5, or a sequence with a sequence identity greater than 90% to SEQ ID NO: 5.

8. The method according to claim 1, wherein decreasing lignin density is achieved by increasing the concentration and/or activity of the polypeptide encoded by the LATE ELONGATED HYPOCOTYL 1 (LHY 1) and the LATE ELONGATED HYPOCOTYL 2 (LHY 2) gene by:
 (i) increasing, promoting or augmenting transcription, translation or expression of the gene;
 (ii) increasing synthesis of the polypeptide encoded by the gene; or
 (iii) decreasing the rate of degradation of the polypeptide encoded by the gene.

9. The method according to claim 1, wherein the genetic construct encodes an exogenous gene, wherein said exogenous gene is is LATE ELONGATED HYPOCOTYL 1 and LATE ELONGATED HYPOCOTYL 2 gene.

10. A tobacco product comprising lignin-reduced tobacco obtained from a genetically modified tobacco plant or progeny thereof, which plant exhibits increased concentration and/or activity of a polypeptide encoded by an LHY 1 and LHY 2 gene, said gene comprising SEQ ID NO:1 or SEQ ID NO:3 or a sequence with 90% sequence identity thereto.

11. The tobacco product according to claim 10, wherein the tobacco product is a smokeless tobacco product, or an oral tobacco product deliverable by the mouth.

12. A transgenic plant comprising a genetic construct comprising LATE ELONGATED HYPOCOTYL 1 and LATE ELONGATED HYPOCOTYL 2, and wherein the plant exhibits an increase in the density of the lignin relative to the density of lignin in a plant lacking the construct.

13. The plant of claim 12, wherein the plant is selected from a family selected from the group consisting of Brassicaceae, Poales, and Solanaceae.

14. A transgenic plant or progeny thereof, comprising a genetic construct designed to modulate the concentration and/or activity of a LATE ELONGATED HYPOCOTYL 1 (LHY 1) and/or a LATE ELONGATED HYPOCOTYL 2 (LHY 2) gene wherein said LHY 1 gene comprises a nucleic acid sequence as set forth in SEQ ID NO: 1 or a sequence with at least 90% sequence identity thereto, and said LHY 2 gene comprises a nucleic acid sequence as set forth in SEQ ID NO: 3 or a sequence with at least 90% sequence identity thereto.

15. The plant of claim 13, wherein the at least one construct comprises the nucleotide sequence of SEQ ID NO:1 or SEQ ID NO: 3, or a nucleic acid sequence with at least 90% sequence identity to SEQ ID NO:1 or SEQ ID NO: 3.

16. A method of modulating the density of lignin in a test plant compared to the corresponding wild-type plant cultured under the same conditions, the method comprising:
 introducing into said test plant or an ancestor thereof a polynucleotide construct comprising an RNAi nucleotide sequence; and thereafter,
 regenerating said plant,
 wherein said RNAi nucleotide comprises at least 20 consecutive bases with a sequence identity greater than 90% to SEQ ID NO: 1 and to SEQ ID NO: 3 wherein lignin density increases in said test plant or ancestor thereof.

17. The method of claim 16, wherein said RNAi nucleotide sequence is as set out in SEQ ID NO:5 or a sequence with a sequence identity greater than 90% to SEQ ID NO:5.

18. The method of claim 16, wherein said target sequence has 30 consecutive bases with a sequence identity greater than 90% to LATE ELONGATED HYPOCOTYL 1 (LHY1) and LATE ELONGATED HYPOCOTYL 2 (LHY2) genes, wherein said LHY1 gene comprises a nucleic acid sequence as set forth in SEQ ID NO: 1 or a sequence with greater than 90% sequence identity thereto and said LHY2 gene comprises a nucleic acid sequence as set forth in SEQ ID NO: 3 or a sequence with greater than 90% sequence identity thereto.

19. The method of claim 16, wherein said target sequence has 40 consecutive bases with a sequence identity greater than 90% to LATE ELONGATED HYPOCOTYL 1 (LHY1) and LATE ELONGATED HYPOCOTYL 2 (LHY2) genes, wherein said LHY1 gene comprises a nucleic acid sequence as set forth in SEQ ID NO: 1 or a sequence with greater than 90% sequence identity thereto and said LHY2 gene comprises a nucleic acid sequence as set forth in SEQ ID NO: 3 or a sequence with greater than 90% sequence identity thereto.

20. A genetic construct, comprising:
 an RNAi sequence having 20 consecutive bases with a sequence identity greater than 90% to LATE ELONGATED HYPOCOTYL 1 (LHY1) and LATE ELONGATED HYPOCOTYL 2 (LHY2) genes, wherein said LHY1 gene comprises a nucleic acid sequence as set forth in SEQ ID NO: 1 or a sequence with greater than 90% sequence identity thereto and said LHY2 gene comprises a nucleic acid sequence as set forth in SEQ ID NO: 3 or a sequence with greater than 90% sequence identity thereto; and
 a heterologous promoter wherein said heterologous promoter is operantly linked to said sequence.

21. The genetic construct of claim 20, where said RNAi sequence is as set out in SEQ ID NO: 5 or a sequence with a sequence identity greater than 90% to SEQ ID NO: 5.

22. A genetic construct, comprising:
 an RNAi sequence having a sequence identity greater than 90% to at least 20 continuous bases from position 37 to 80 of LATE ELONGATED HYPOCOTYL 1 (LHY1), wherein said LHY1 sequence comprises a nucleic acid sequence as set forth in SEQ ID NO: 1 or a sequence with greater than 90% sequence identity thereto; and
a heterologous promoter wherein said heterologous promoter is operantly joined to said sequence.

* * * * *

SEQUENCE LISTING

<160> NUMBER OF SEQ ID NOS: 7

<210> SEQ ID NO 1
<211> LENGTH: 2379
<212> TYPE: DNA
<213> ORGANISM: Populus sp.

<400> SEQUENCE: 1

| | | | | | | |
|---|---|---|---|---|---|---|
| atgggttgtg | ggataaagtg | gcacaattgg | attactgagt | tggagaagga | ggctgttgct | 60 |
| aaaggtgttc | cgataggaaa | agcacttgaa | atagacattc | caccaccacg | tcccaaaagg | 120 |
| aaaccaagca | atccttatcc | tcgaaagaca | ggtgtgggtc | ctcccgcatc | acaggcagga | 180 |
| gcaaaggatg | gaaagctttt | aacttcaact | tcttctccac | attgtaggaa | agttttagat | 240 |
| ttggagaaag | aaccacgtcc | tgagaaacct | aatggagatg | agaggccaac | caatgctaag | 300 |
| gaaaatcagg | atgacaattg | ctcagaagta | tttacccttc | tccaagaagc | tcattgttcc | 360 |
| tctgtagctt | cagtcaacaa | aaattgtgta | ccagcactag | aggttctcaa | aaagactagc | 420 |
| tctttcaggg | agtttgtacc | ttcaccgaag | aagggaaatc | atgatgcatg | caatgaatcc | 480 |
| tttatcactg | tcgagcatga | agcaaatcaa | aagttggaca | gctctgatgc | caatcagaca | 540 |
| gttttggata | tggcactgt | taaagcttca | aaatcagaaa | attcttgctc | tttgcatgag | 600 |
| atattgtttc | agcaaaagaa | atcagatgat | tttattggat | cattgccaac | agatgagatg | 660 |
| aaagccatgc | agaactatcc | aaggcatgtc | cctgtacacg | ttctagatgg | gagcctggga | 720 |
| acatgtatgg | aaactccctc | ggatttgtca | tttcaggatt | ccatgtttca | tccagtagga | 780 |
| gatattccag | cgtgtcctat | tttatactca | catcctactg | gatccactac | cactgatcat | 840 |
| ccaactaatt | tgccaagatc | tctatgcat | caatcatttc | cattttttcc | tcctccattt | 900 |
| accccaactc | atcataatca | agatgactac | agatcatttc | tccacatatc | ctccacattt | 960 |
| tcgagtcccg | ttgtatctac | tctgctacaa | aacccggcag | cccatgctgc | agcaagcttt | 1020 |
| gcagctacct | tttggcccta | tggaaatgtg | gagagttccg | cagattctcc | agcatgtgcc | 1080 |
| caagaaggtt | tccaatcggg | gcaaataaac | tctgctccca | gtatggcagc | tattgctgct | 1140 |
| gctacagtgg | cagcagcaac | tgcatggtgg | gcagcacatg | gactacttcc | catatgtgct | 1200 |
| cctcttcaca | ctgcctttgc | ctgccctcct | gcttctgcaa | ctgcaattca | gtctgcggat | 1260 |
| actgatcaag | ttcctccagc | caagccagaa | aggaaggaaa | caactcctga | taatcctcct | 1320 |
| ttgcaaggtc | aaatacagga | cctggagcac | tctgaagctg | tgcaagctca | aaactctgca | 1380 |
| tcaaaaccac | caacgttgtc | atcatcagat | tctgaagaga | gtggaggcac | aaagctaaac | 1440 |
| actgcaccaa | aagttactga | tcacgagtta | aattcaaaag | ctcctgaggt | ccaggattca | 1500 |
| ggcaaaacaa | agagcagaaa | acaggttgac | cgttcttcat | gtggttcaaa | tacaccatct | 1560 |
| agcagtgaaa | ttgagacaga | tgcattagag | aagaatgaga | aaggcaagga | agagccaaaa | 1620 |
| gaagctgatg | caaatcatcc | agcctctgag | ttgaactgtc | gccgcagcag | aagtagcagc | 1680 |
| agcatgagtg | attcgtggaa | agaggtctcc | gaagaggggc | ggctggcatt | tcaagcacta | 1740 |
| ttcaccagag | agagattgcc | ccagagcttc | tcacctccac | atgatctgaa | gagtaagatg | 1800 |
| caccagaagg | aagatactga | agaaaagaaa | aatccagatg | agaaagatgg | agatgcgtca | 1860 |
| ctgttagatc | tcaacagcaa | aacatggggt | tactgctctg | gctatcaaga | aggggagaaa | 1920 |
| aatgctgtag | tgcctagatg | tgtaaacgat | ggggaggaag | ggctgctgac | tattggactt | 1980 |
| ggacatggaa | atctgaaggc | tcatctaacc | ggatttaaac | cttacaaaag | gtgttcactg | 2040 |
| gaggccaaag | aaagcaggat | gggaaccact | ggtggccagg | gcgaggagaa | aggccccaag | 2100 |

```
aggttacgtt tggaaaggga agcttcagtt tgatacttga tactgcatgc ttaaacaagg      2160 gaaaacctt  gttttgtat  gtaatttcta attttctccc ttgtctatca ttccgttcat     2220
gtttaaatta gaggaacggc aacccaggag acttttcgtg taagtgtgtg tgcttatata     2280
tcagacattg gcttatttac tttcttgaac ccatgactgc agttaagtat ccatcaaaag     2340
acctagataa gaacttaaga agcattaagt attgaattg                           2379
```

<210> SEQ ID NO 2
<211> LENGTH: 768
<212> TYPE: PRT
<213> ORGANISM: Populus sp.

<400> SEQUENCE: 2

```
Met Asp Thr Tyr Ser Ala Gly Glu Asp Leu Val Ile Lys Thr Arg Lys
1               5                   10                  15

Pro Tyr Thr Ile Thr Lys Gln Arg Glu Arg Trp Thr Glu Glu Glu His
                20                  25                  30

Asn Arg Phe Leu Glu Ala Leu Lys Leu Tyr Gly Arg Ala Trp Gln Arg
            35                  40                  45

Ile Glu Glu His Ile Gly Thr Lys Thr Ala Val Gln Ile Arg Ser His
        50                  55                  60

Ala Gln Lys Phe Phe Ser Lys Leu Glu Lys Glu Ala Val Ala Lys Gly
65                  70                  75                  80

Val Pro Ile Gly Gln Ala Leu Glu Ile Asp Ile Pro Pro Arg Pro
                85                  90                  95

Lys Arg Lys Pro Ser Asn Pro Tyr Pro Arg Lys Thr Gly Val Gly Pro
            100                 105                 110

Pro Ala Ser Gln Ala Gly Ala Lys Asp Gly Lys Leu Leu Thr Ser Thr
        115                 120                 125

Ser Ser Pro His Cys Arg Lys Val Leu Asp Leu Glu Lys Glu Pro Arg
    130                 135                 140

Pro Glu Lys Pro Asn Gly Asp Glu Arg Pro Thr Asn Ala Lys Glu Asn
145                 150                 155                 160

Gln Asp Asp Asn Cys Ser Glu Val Phe Thr Leu Leu Gln Glu Ala His
                165                 170                 175

Cys Ser Ser Val Ala Ser Val Asn Lys Asn Cys Val Pro Ala Leu Glu
            180                 185                 190

Val Leu Lys Lys Thr Ser Ser Phe Arg Glu Phe Val Pro Ser Pro Lys
        195                 200                 205

Lys Gly Asn Asp Asp Ala Cys Asn Glu Ser Phe Ile Thr Val Glu His
    210                 215                 220

Glu Ala Asn Gln Lys Leu Asp Ser Ser Asp Ala Asn Gln Thr Val Leu
225                 230                 235                 240

Asp Asn Gly Thr Val Lys Ala Ser Lys Ser Glu Asn Ser Cys Ser Leu
                245                 250                 255

His Glu Ile Leu Phe Gln Gln Lys Lys Ser Asp Asp Phe Ile Gly Ser
            260                 265                 270

Leu Pro Thr Asp Glu Met Gln Ala Met Gln Asn Tyr Pro Arg His Val
        275                 280                 285

Pro Val His Val Leu Asp Gly Ser Leu Gly Thr Cys Ile Glu Thr Pro
    290                 295                 300

Ser Asp Leu Ser Phe Gln Asp Ser Met Phe His Pro Val Gly Asp Ile
305                 310                 315                 320
```

```
Pro Ala Cys Pro Ile Leu Tyr Ser His Pro Ala Gly Ser Thr Thr Thr
                325                 330                 335

Asp His Pro Thr Asn Leu Pro Arg Ser Ser Met His Gln Ser Phe Pro
        340                 345                 350

Phe Phe Pro Pro Pro Phe Thr Pro Thr His His Asn Gln Asp Asp Tyr
            355                 360                 365

Arg Ser Phe Leu His Ile Ser Ser Thr Phe Ser Ser Pro Val Val Ser
370                 375                 380

Thr Leu Leu Gln Asn Pro Ala Ala His Ala Ala Ser Phe Ala Ala
385                 390                 395                 400

Thr Phe Trp Pro Tyr Gly Asn Val Glu Ser Ser Ala Asp Ser Pro Ala
                405                 410                 415

Cys Ala Gln Glu Gly Phe Gln Ser Gly Gln Ile Asn Ser Ala Pro Ser
                420                 425                 430

Met Ala Ala Ile Ala Ala Ala Thr Val Ala Ala Ala Thr Ala Trp Trp
            435                 440                 445

Ala Ala His Gly Leu Leu Pro Ile Cys Ala Pro Leu His Thr Ala Phe
        450                 455                 460

Ala Cys Pro Pro Ala Ser Ala Thr Ala Ile Gln Ser Ala Asp Thr Asp
465                 470                 475                 480

Gln Val Pro Pro Ala Lys Pro Glu Arg Lys Glu Thr Thr Pro Asp Asn
                485                 490                 495

Pro Pro Leu Gln Gly Gln Ile Gln Asp Leu Glu His Ser Glu Ala Val
                500                 505                 510

Gln Ala Gln Asn Ser Ala Ser Lys Pro Pro Thr Leu Ser Ser Ser Asp
            515                 520                 525

Ser Glu Glu Ser Gly Gly Thr Lys Leu Asn Thr Gly Pro Lys Val Thr
530                 535                 540

Asp Asp Glu Leu Asn Ser Lys Ala Pro Glu Val Gln Asp Ser Gly Lys
545                 550                 555                 560

Thr Lys Ser Arg Lys Gln Val Asp Arg Ser Ser Cys Gly Ser Asn Thr
                565                 570                 575

Pro Ser Ser Ser Glu Ile Glu Thr Asp Ala Leu Glu Lys Thr Glu Lys
            580                 585                 590

Gly Lys Glu Glu Pro Lys Glu Ala Asp Ala Asn His Pro Ala Ser Glu
        595                 600                 605

Ser Asn Cys Arg Arg Ser Arg Ser Ser Ser Met Ser Asp Ser Trp
610                 615                 620

Lys Glu Val Ser Glu Glu Gly Arg Leu Ala Phe Gln Ala Leu Phe Thr
625                 630                 635                 640

Arg Glu Ile Leu Pro Gln Ser Phe Ser Pro Pro His Asp Leu Lys Ser
                645                 650                 655

Lys Met His Gln Lys Glu Asp Thr Glu Glu Lys Lys Asn Pro Asp Glu
                660                 665                 670

Lys Asp Gly Asp Ala Ser Leu Leu Asp Leu Asn Ser Lys Thr Trp Gly
            675                 680                 685

Tyr Cys Ser Gly Tyr Gln Glu Gly Glu Lys Asn Ala Val Val Pro Arg
        690                 695                 700

Cys Val Asn Asp Gly Glu Gly Leu Leu Thr Ile Gly Leu Gly His
705                 710                 715                 720

Gly Asn Leu Lys Ala His Leu Thr Gly Phe Lys Pro Tyr Lys Arg Cys
                725                 730                 735

Ser Leu Glu Ala Lys Glu Ser Arg Met Ala Thr Thr Gly Gly Gln Gly
```

Glu Glu Lys Gly Pro Lys Arg Leu Arg Leu Glu Arg Glu Ala Ser Val
    740             745             750
            755             760             765

<210> SEQ ID NO 3
<211> LENGTH: 2717
<212> TYPE: DNA
<213> ORGANISM: Populus sp.

<400> SEQUENCE: 3

| | | | | | |
|---|---|---|---|---|---|
| tttctcttgg | gaaggaattg | gagtccatgc | gttcgttttg | ttgtagcgga | acgacggctt | 60 |
| tatttgtagt | attgagtgtt | gcaagaaatg | aagggagatt | tctttttat | cccttgctcg | 120 |
| ttagagagga | tttgaagcag | cgttggctgc | ctaaggtcca | ctaatggaaa | tattctcttc | 180 |
| tggggaagac | ttggttatta | agacaaggaa | accatataca | attaccaagc | aacgagaaag | 240 |
| atggacagag | gaggagcata | gcaggttcct | agaggccttg | aagctctatg | acgagcttg | 300 |
| gcagcgaatt | gaagaacata | ttggtacaaa | gactgtcgtt | cagatcagaa | gtcatgcaca | 360 |
| gaagttcttt | tcaaagttgg | agaaggaggc | tgttgttaaa | ggtgttccaa | taggacaagc | 420 |
| acttgacatt | gacattccac | caccacgtcc | caaaaggaaa | ccaagcaatc | cttatcctcg | 480 |
| aaagataggc | gtgggtcctc | ccgcatcaca | ggtgggagca | aaggatggaa | agcttttaac | 540 |
| ttcagcttct | tttccgtgtt | gtaagcaggt | tttaggcttg | gagaaagaac | cacttcctga | 600 |
| gaaacttaat | ggagatgaga | ggccaaccaa | tgctaaggaa | aatcaggatg | caaattgctc | 660 |
| agaagtattt | tcccttctcc | aagaacctca | ctgttcttct | gtaccttcaa | tcaacaagaa | 720 |
| ttctgtacca | acactagata | ttctcaaaaa | ggctagccct | ttcagggagt | tcgtatcttc | 780 |
| accgaaggag | ggaaatcatg | atgcaagtaa | tcaatcctct | gtcaccgtcg | agcttggagc | 840 |
| aaatcaaaag | ttggacaact | ctgatgtcaa | acaggataac | agcactagtg | agttttcaaa | 900 |
| atcagaaaac | ttttgctctt | tttctgagaa | attgtttcag | caaaagaaat | cagatgattt | 960 |
| tattggagca | ttgcgaacag | atgggatgca | agccatgcag | aactatccaa | ggcatgtccc | 1020 |
| tgtgcatgtt | ctagatggga | gcctgggaac | atgtatgcaa | actcctccct | cagattttc | 1080 |
| gtttcaggaa | tccatgtttc | atccaatagg | agaaattcca | gcatgtccta | atttatattc | 1140 |
| acatcctgct | gcatccaaaa | ccactgatca | tccaaatatt | tcaccgagat | cctctatgca | 1200 |
| tcaatcattt | ccaagttttc | ctcctcccett | taccccaact | catcataatc | aagatgacta | 1260 |
| cagatctttc | ctccacatat | cctccacatt | ttcaagcctc | gttgtatctt | ctctgctaca | 1320 |
| aaaccccggca | gcccatgctg | cagcaagctt | tgcatctacc | ttttggccct | atggaaatgt | 1380 |
| ggagagttct | gcggattctc | cagcatgtgc | ccaaggaggt | ttccaatcca | ggcaattgaa | 1440 |
| ctctgctcct | agtatggcag | ctattgttgc | tgctacagtg | gcagcagcaa | ccgcatggtg | 1500 |
| gacagcgcat | ggactacttc | ccatgtgtgc | ccctcttcat | acctcgtttg | cctgccctcc | 1560 |
| tgcatctgca | actgcaattc | agtctgaaac | agctgaaaat | ccttctttgc | agggacaaat | 1620 |
| acagggccca | gagcacactg | aagcattgca | agctcaaaac | tcagcatcta | aatcaccaaa | 1680 |
| gataacatca | tcagactctg | aagagagcgg | aggcccaaag | ctaaatactg | gaccagaagt | 1740 |
| tattgatcat | gagttgacta | caaaacctca | cgaggtccag | gattcaagca | aaacaaagag | 1800 |
| cagaaaactg | attgaccgtt | cttcatgtgg | ttcaaacaca | ccttctagca | gtgaaataga | 1860 |
| gacagatgca | ttagagaagg | ctgagaaagg | cacggaagag | ccaaaagaag | atgatgcaaa | 1920 |
| tcatccagct | tccgaatcta | gctctcgcca | cagcagaagc | agtagcagca | tgaatgattc | 1980 |

-continued

```
atggaaagag gtctccgaag aggggcggct ggcatttcaa gcactcttcg ctagagaggt    2040
attgccccag agcttctcac ctccacatga tctgaagagt aagatgcacc agaatgaaga    2100
tgctggagaa aagaaagatg cagatgagaa agatggagat gcatcactga taaatctcaa    2160
cagtaaaacg tgggagtgct gctctggtca tcaagaaggg gagaaaaatg ctttgtctag    2220
atgtgaaaac tatggggagg aggagctgct gacgattggg cttggacatg aaagcttaa     2280 ggttcgtcga accggattta aaccttacaa aaggtgttca ctggaggcca agaaagcag     2340 gaccggaacc ggcagcggcc agggcgagga gaaaggcccc aagaggttac gtttggaagg    2400
agaagcttca gtttgatact tgatattgct tgcttgaata agggaaaacc tttgtttttg    2460
catgtaattt ataatatcct cgcttgccta tcattccttt tatgtttaaa ttagagtatc    2520
tgcaacccac aagacttgtc gtgtaagtgt gtgtactata tgtcgacatt ggcttattta    2580
ctttcttgaa cccattaccg catttaagaa ctccgttaaa tagacgtaga taagaactta    2640
agaaccatta gaaccattaa gtattgaatt ggctttccac ggcccttttc ctccaaagtt    2700
cataattatt ttctaac                                                   2717
```

<210> SEQ ID NO 4
<211> LENGTH: 764
<212> TYPE: PRT
<213> ORGANISM: Populus sp.

<400> SEQUENCE: 4

```
Met Glu Ile Phe Ser Ser Gly Glu Asp Leu Val Ile Lys Thr Arg Lys
1               5                   10                  15

Pro Tyr Thr Ile Thr Lys Gln Arg Glu Arg Trp Thr Asp Glu Glu His
            20                  25                  30

Ser Arg Phe Leu Glu Ala Leu Lys Leu Tyr Gly Arg Ala Trp Gln Arg
        35                  40                  45

Ile Glu Glu His Ile Gly Thr Lys Thr Val Val Gln Ile Arg Ser His
    50                  55                  60

Ala Gln Lys Phe Phe Ser Lys Leu Glu Lys Glu Ala Ile Val Lys Gly
65                  70                  75                  80

Val Pro Ile Gly Gln Ala Leu Asp Ile Asp Pro Pro Pro Arg Pro
                85                  90                  95

Lys Arg Lys Pro Ser Asn Pro Tyr Pro Arg Lys Ile Gly Val Gly Pro
            100                 105                 110

Pro Ala Ser Gln Val Gly Ala Lys Asp Gly Lys Leu Leu Thr Ser Ala
        115                 120                 125

Ser Phe Pro Cys Cys Lys Gln Val Leu Gly Leu Glu Lys Glu Pro Leu
    130                 135                 140

Pro Glu Lys Leu Asn Gly Asn Glu Arg Pro Thr Asp Ala Lys Glu Asn
145                 150                 155                 160

Gln Asp Asp Asn Cys Ser Glu Val Phe Ser Leu Leu Gln Glu Pro His
                165                 170                 175

Cys Ser Ser Val Pro Ser Val Asn Lys Asn Ser Val Pro Thr Leu Asp
            180                 185                 190

Ile Leu Lys Lys Ala Ser Pro Phe Arg Glu Phe Val Ser Ser Pro Lys
        195                 200                 205

Glu Gly Asn His Asp Ala Ser Asn Gln Ser Ser Val Thr Val Asp Leu
    210                 215                 220

Gly Ala Asn Gln Lys Leu Asp Asn Ser Asp Val Lys Gln Asp Asn Ser
225                 230                 235                 240
```

-continued

Thr Ser Glu Phe Ser Lys Ser Glu Asn Phe Cys Ser Phe Ser Glu Lys
                    245                 250                 255

Leu Phe Gln Gln Lys Lys Ser Asp Asp Phe Ile Gly Ala Leu Arg Thr
            260                 265                 270

Asp Gly Met Gln Ala Met Gln Asn Tyr Pro Arg His Val Pro Val His
            275                 280                 285

Val Leu Asp Gly Ser Leu Gly Thr Cys Met Gln Thr Pro Pro Ser Asp
        290                 295                 300

Phe Ser Phe Gln Glu Ser Ile Phe His Pro Ile Gly Glu Ile Pro Ala
305                 310                 315                 320

Cys Pro Asn Leu Tyr Ser His Pro Ala Ala Ser Lys Thr Thr Asp His
                325                 330                 335

Pro Asn Ile Ser Pro Arg Ser Ser Met His Gln Ser Phe Pro Ser Phe
                340                 345                 350

Pro Pro Pro Phe Thr Pro Thr His His Asn Gln Asp Asp Tyr Arg Ser
            355                 360                 365

Phe Leu His Met Ser Ser Thr Phe Ser Ser Leu Val Val Ser Ser Leu
        370                 375                 380

Leu Gln Asn Pro Ala Ala His Ala Ala Ala Ser Phe Ala Ser Thr Phe
385                 390                 395                 400

Trp Pro Tyr Gly Asn Val Glu Ser Ser Ala Asp Ser Pro Ala Cys Ala
                405                 410                 415

Gln Gly Gly Phe Gln Ser Arg Gln Leu Asn Ser Ala Pro Ser Met Ala
            420                 425                 430

Ala Ile Val Ala Ala Thr Val Ala Ala Ala Thr Ala Trp Trp Thr Ala
        435                 440                 445

His Gly Leu Leu Pro Met Cys Ala Pro Leu His Thr Ser Phe Ala Cys
    450                 455                 460

Pro Pro Ala Ser Ala Thr Ala Ile Gln Ser Val Asp Thr Gly Gln Val
465                 470                 475                 480

Ser Ala Thr Lys Thr Glu Arg Lys Glu Thr Ala Glu Asn Pro Ser Leu
                485                 490                 495

Gln Gly Gln Ile Gln Asp Gln Glu His Thr Glu Ala Leu Gln Ala Gln
            500                 505                 510

Asn Ser Ala Ser Lys Ser Pro Lys Ile Thr Ser Ser Asp Ser Glu Glu
        515                 520                 525

Ser Gly Gly Pro Gln Leu Asn Thr Arg Pro Glu Val Ile Asp His Glu
    530                 535                 540

Leu Thr Thr Lys Pro His Glu Val Gln Asp Ser Ser Lys Thr Lys Ser
545                 550                 555                 560

Arg Lys Leu Ile Asp Arg Ser Ser Cys Gly Ser Asn Thr Pro Ser Ser
                565                 570                 575

Ser Glu Ile Glu Thr Asp Ala Leu Glu Lys Ala Glu Lys Gly Thr Glu
            580                 585                 590

Glu Pro Lys Glu Asp Asp Ala Asn His Pro Ala Ser Glu Ser Ser Ser
        595                 600                 605

Arg His Ser Arg Ser Ser Ser Met Asn Asp Ser Trp Lys Glu Val
    610                 615                 620

Ser Glu Glu Gly Arg Leu Ala Phe Gln Thr Leu Phe Ala Arg Glu Val
625                 630                 635                 640

Leu Pro Gln Ser Phe Ser Pro Pro His Asp Leu Lys Ser Lys Met His
                645                 650                 655

Gln Asn Glu Asp Ala Gly Glu Lys Lys Asp Ala Asp Glu Lys Asp Gly

```
                    660              665              670
Asp Ala Ser Leu Ile Asn Leu Asn Thr Lys Thr Trp Glu Cys Cys Ser
            675              680              685

Gly His Gln Glu Gly Glu Lys Asn Ala Leu Ser Arg Cys Glu Asn Tyr
        690              695              700

Gly Glu Glu Gly Leu Leu Thr Ile Gly Leu Gly His Gly Lys Leu Lys
705              710              715              720

Val Arg Arg Thr Gly Phe Lys Pro Tyr Lys Arg Cys Ser Leu Glu Ala
                725              730              735

Lys Glu Ser Arg Thr Gly Thr Gly Ser Gly Gln Gly Glu Glu Lys Gly
                740              745              750

Pro Lys Arg Leu Arg Leu Glu Gly Glu Ala Ser Val
            755              760

<210> SEQ ID NO 5
<211> LENGTH: 255
<212> TYPE: DNA
<213> ORGANISM: Unknown
<220> FEATURE:
<223> OTHER INFORMATION: RNAi molecule

<400> SEQUENCE: 5
atggaaatat tctcttctgg ggaagacttg gttattaaga caaggaaacc atatacaatt      60
accaagcaac gagaaagatg gacagaggag gagcatagca ggttcctaga ggccttgaag     120
ctctatggac gagcttggca gcgaattgaa gaacatattg gtacaaagac tgtcgttcag     180
atcagaagtc atgcacagaa gttcttttca aagttggaga aggaggctgt tgttaaaggt     240
gttccaatag gacaa                                                      255

<210> SEQ ID NO 6
<211> LENGTH: 49
<212> TYPE: DNA
<213> ORGANISM: Artificial Sequence
<220> FEATURE:
<223> OTHER INFORMATION: Forward primer for LHY1 and LHY2

<400> SEQUENCE: 6
ggggacaagt ttgtacaaaa aagcaggcat ggaaatattc tcttctggg                   49

<210> SEQ ID NO 7
<211> LENGTH: 49
<212> TYPE: DNA
<213> ORGANISM: Artificial Sequence
<220> FEATURE:
<223> OTHER INFORMATION: Reverse primer for LHY1 and LHY2

<400> SEQUENCE: 7
ggggaccact ttgtacaaga aagctgggtt tgtcctattg gaacacctt                    49
```